United States Patent
Cooper et al.

(10) Patent No.: US 9,671,358 B2
(45) Date of Patent: Jun. 6, 2017

(54) ROUTE EXAMINING SYSTEM AND METHOD

(71) Applicant: General Electric Company, Schenectady, NY (US)

(72) Inventors: Jared Klineman Cooper, Melbourne, FL (US); Ajith Kuttannair Kumar, Erie, PA (US); Joseph Forrest Noffsinger, Lee's Summit, MO (US)

(73) Assignee: General Electric Company, Schenectady, NY (US)

( * ) Notice: Subject to any disclaimer, the term of this patent is extended or adjusted under 35 U.S.C. 154(b) by 564 days.

(21) Appl. No.: 14/155,454

(22) Filed: Jan. 15, 2014

(65) Prior Publication Data

US 2014/0125356 A1 May 8, 2014

Related U.S. Application Data

(63) Continuation of application No. PCT/US2013/054284, filed on Aug. 9, 2013.
(Continued)

(51) Int. Cl.
*G01N 27/02* (2006.01)
*B61K 9/10* (2006.01)
*B61L 23/04* (2006.01)

(52) U.S. Cl.
CPC ............. *G01N 27/023* (2013.01); *B61K 9/10* (2013.01); *B61L 23/044* (2013.01)

(58) Field of Classification Search
CPC .. B61K 9/08; B61K 9/10; B61L 23/04; B61L 23/041; B61L 23/042; B61L 23/044; B61L 23/045; B61L 23/047; B61L 23/048
See application file for complete search history.

(56) References Cited

U.S. PATENT DOCUMENTS

| 2,059,160 A | 10/1934 | Wintsch et al. |
| 2,628,335 A | 2/1953 | Drake et al. |

(Continued)

FOREIGN PATENT DOCUMENTS

| WO | 9530886 | 11/1995 |
| WO | 9601431 | 1/1996 |

(Continued)

OTHER PUBLICATIONS

Popov, Ing. Alexandr; "Automated Ultrasonic Inspection of Rails", Starmans Electronics, s.r.o., Prague, CZ, www.starmans.net, 5 pgs.
(Continued)

*Primary Examiner* — David Gray
*Assistant Examiner* — Michael Harrison
(74) *Attorney, Agent, or Firm* — Global Patent Operation; John A. Kramer

(57) ABSTRACT

A system includes at least one examining module configured to be disposed onboard a vehicle system and a mitigation module. The at least one examining module is configured to identify an identified section of a route being traversed by the vehicle system, with the identified section corresponding to at least one of a potentially damaged section of the route or an actually damaged section of the route. The mitigation module is configured to, responsive to an identification by the at least one examining module of the identified section of the route, automatically perform a mitigation action corresponding to the identified section of the route.

20 Claims, 6 Drawing Sheets

Related U.S. Application Data

(60) Provisional application No. 61/860,469, filed on Jul. 31, 2013, provisional application No. 61/860,496, filed on Jul. 31, 2013, provisional application No. 61/729,188, filed on Nov. 21, 2012, provisional application No. 61/681,843, filed on Aug. 10, 2012.

(56) References Cited

U.S. PATENT DOCUMENTS

| | | |
|---|---|---|
| 3,016,464 A | 1/1962 | Bailey et al. |
| 3,137,756 A | 6/1964 | Gunther et al. |
| 3,393,600 A | 7/1968 | Bess et al. |
| 3,517,307 A | 6/1970 | Wallen et al. |
| 3,562,419 A | 2/1971 | Stewart et al. |
| 3,589,815 A | 6/1971 | Hosterman |
| 3,594,912 A | 7/1971 | Sauterel |
| 3,604,359 A | 9/1971 | Doorley et al. |
| 3,633,010 A | 1/1972 | Svetlichny |
| 3,696,243 A | 10/1972 | Risely |
| 3,821,558 A | 6/1974 | Mansfield |
| 3,821,932 A | 7/1974 | Theurer et al. |
| 3,828,440 A | 8/1974 | Plasser et al. |
| 3,850,390 A | 11/1974 | Geiger et al. |
| 3,864,039 A | 2/1975 | Wilmarth |
| 3,870,952 A | 3/1975 | Sibley |
| 3,875,865 A | 4/1975 | Plasser et al. |
| 3,896,665 A | 7/1975 | Goel |
| 3,924,461 A | 12/1975 | Stover |
| 3,937,068 A | 2/1976 | Joy |
| 3,960,005 A | 6/1976 | Vezina |
| 3,962,908 A | 6/1976 | Joy |
| 3,974,991 A | 8/1976 | Geiger |
| 3,987,989 A | 10/1976 | Geiger |
| 3,995,560 A | 12/1976 | Mackintosh |
| 4,005,601 A | 2/1977 | Botello |
| 4,022,408 A | 5/1977 | Staples |
| 4,040,738 A | 8/1977 | Wagner |
| 4,044,594 A | 8/1977 | Davidson et al. |
| 4,069,590 A | 1/1978 | Effinger |
| 4,117,529 A | 9/1978 | Ehrlich et al. |
| 4,143,553 A | 3/1979 | Hendricks et al. |
| 4,145,018 A | 3/1979 | Muratore et al. |
| 4,155,176 A | 5/1979 | Goel et al. |
| 4,165,648 A | 8/1979 | Pagano |
| 4,173,073 A | 11/1979 | Fukazawa et al. |
| 4,174,636 A | 11/1979 | Pagano |
| 4,181,430 A | 1/1980 | Ando et al. |
| 4,198,164 A | 4/1980 | Cantor |
| 4,207,569 A | 6/1980 | Meyer |
| 4,222,275 A | 9/1980 | Marshall et al. |
| 4,229,978 A | 10/1980 | Marshall et al. |
| 4,235,112 A | 11/1980 | Kaiser |
| 4,259,018 A | 3/1981 | Poirier |
| 4,288,855 A | 9/1981 | Panetti |
| 4,306,694 A | 12/1981 | Kuhn |
| 4,383,448 A | 5/1983 | Fujimoto et al. |
| 4,389,033 A | 6/1983 | Hardman |
| 4,391,134 A | 7/1983 | Hansmann et al. |
| 4,417,466 A | 11/1983 | Panetti |
| 4,417,522 A | 11/1983 | Bock et al. |
| 4,429,576 A | 2/1984 | Norris |
| 4,430,615 A | 2/1984 | Calvert |
| 4,457,178 A | 7/1984 | Meignan et al. |
| 4,467,430 A | 8/1984 | Even et al. |
| 4,468,966 A | 9/1984 | Bradshaw |
| 4,487,071 A | 12/1984 | Morris et al. |
| 4,490,038 A | 12/1984 | Riessberger et al. |
| 4,531,837 A | 7/1985 | Panetti |
| 4,538,061 A | 8/1985 | Jaquet |
| 4,541,182 A | 9/1985 | Panetti |
| 4,548,070 A | 10/1985 | Panetti |
| 4,577,494 A | 3/1986 | Jaeggi |
| 4,578,665 A | 3/1986 | Yang |
| 4,593,569 A | 6/1986 | Joy |
| 4,609,870 A | 9/1986 | Hocking et al. |
| 4,615,218 A | 10/1986 | Pagano |
| 4,625,412 A | 12/1986 | Bradshaw |
| 4,654,973 A | 4/1987 | Worthy |
| 4,655,142 A | 4/1987 | Bock et al. |
| 4,662,224 A | 5/1987 | Turbe |
| 4,689,995 A | 9/1987 | Turbe |
| 4,691,565 A | 9/1987 | Theurer |
| 4,700,223 A | 10/1987 | Shoutaro et al. |
| 4,700,574 A | 10/1987 | Turbe |
| 4,723,738 A | 2/1988 | Franke |
| 4,728,063 A | 3/1988 | Auer et al. |
| 4,735,384 A | 4/1988 | Elliott |
| 4,741,207 A | 5/1988 | Spangler |
| 4,763,526 A | 8/1988 | Pagano |
| 4,886,226 A | 12/1989 | Frielinghaus |
| 4,915,504 A | 4/1990 | Thurston |
| 4,932,618 A | 6/1990 | Davenport et al. |
| 4,979,392 A | 12/1990 | Guinon |
| 4,986,498 A | 1/1991 | Nayer et al. |
| 5,009,014 A | 4/1991 | Leach |
| 5,036,594 A | 8/1991 | Jordan et al. |
| 5,086,591 A | 2/1992 | Panetti |
| 5,094,004 A | 3/1992 | Wooten |
| 5,101,358 A | 3/1992 | Panetti |
| 5,134,808 A | 8/1992 | Panetti |
| 5,140,776 A | 8/1992 | Isdahl et al. |
| 5,161,891 A | 11/1992 | Austill |
| 5,199,176 A | 4/1993 | Eglseer et al. |
| 5,203,089 A | 4/1993 | Centil et al. |
| 5,253,830 A | 10/1993 | Durchschlag et al. |
| 5,275,051 A | 1/1994 | De Beer |
| 5,301,548 A | 4/1994 | Theurer |
| 5,339,692 A | 8/1994 | Ivachev et al. |
| 5,341,683 A | 8/1994 | Searle |
| 5,353,512 A | 10/1994 | Lichtberger et al. |
| 5,386,727 A | 2/1995 | Searle |
| 5,419,196 A | 5/1995 | Havira et al. |
| 5,429,329 A | 7/1995 | Swanson et al. |
| 5,433,111 A | 7/1995 | Hershey et al. |
| 5,452,222 A | 9/1995 | Swanson et al. |
| 5,459,663 A | 10/1995 | Franke |
| 5,475,597 A | 12/1995 | Buck |
| 5,522,265 A | 6/1996 | Jaeggi |
| 5,529,267 A | 6/1996 | Boyle et al. |
| 5,574,224 A | 11/1996 | Jaeggi |
| 5,578,758 A | 11/1996 | Havira et al. |
| 5,579,013 A | 11/1996 | Hershey et al. |
| 5,598,782 A | 2/1997 | Marriott et al. |
| 5,605,099 A | 2/1997 | Bradshaw et al. |
| 5,613,442 A | 3/1997 | Ahola et al. |
| 5,623,244 A | 4/1997 | Cooper |
| 5,627,508 A | 5/1997 | Anderson et al. |
| 5,628,479 A | 5/1997 | Ballinger |
| 5,636,026 A | 6/1997 | Hubin et al. |
| 5,680,054 A | 10/1997 | Gauthier |
| 5,698,977 A | 12/1997 | Fulton et al. |
| 5,719,771 A | 2/1998 | Buck et al. |
| 5,721,685 A | 2/1998 | Brown et al. |
| 5,743,495 A | 4/1998 | Ali et al. |
| 5,751,144 A | 5/1998 | Weischedel |
| 5,756,903 A | 5/1998 | Norby et al. |
| 5,769,364 A | 6/1998 | Cipollone |
| 5,777,891 A | 7/1998 | Mackay et al. |
| 5,786,535 A | 7/1998 | Ishiyama et al. |
| 5,786,750 A | 7/1998 | Cooper |
| 5,791,063 A | 8/1998 | Gamble et al. |
| 5,804,731 A | 9/1998 | Jaeggi |
| 5,867,404 A | 2/1999 | Bryan |
| 5,924,654 A | 7/1999 | Anderson |
| 5,956,664 A | 9/1999 | Bryan |
| 5,970,438 A | 10/1999 | Boyle et al. |
| 5,986,547 A | 11/1999 | Boedigheimer et al. |
| 5,987,979 A | 11/1999 | Bryan |
| 5,992,241 A | 11/1999 | Beli et al. |
| 6,026,687 A | 2/2000 | Jury |
| 6,044,698 A | 4/2000 | Bryan |
| 6,055,862 A | 5/2000 | Martens |

(56) References Cited

U.S. PATENT DOCUMENTS

| | | |
|---|---|---|
| 6,064,428 A | 5/2000 | Cunningham et al. |
| 6,102,340 A | 8/2000 | Basta et al. |
| 6,119,353 A | 9/2000 | Gr.o slashed.nskov |
| 6,262,573 B1 | 7/2001 | Wojnarowski et al. |
| 6,324,912 B1 | 12/2001 | Wooh |
| 6,347,265 B1 | 2/2002 | Bidaud |
| 6,349,653 B1 | 2/2002 | Siedlarczyk |
| 6,356,299 B1 | 3/2002 | Trosino et al. |
| 6,373,403 B1 | 4/2002 | Korver et al. |
| 6,405,141 B1 | 6/2002 | Carr et al. |
| 6,415,522 B1 | 7/2002 | Ganz |
| 6,416,020 B1 | 7/2002 | Gronskov |
| 6,417,765 B1 | 7/2002 | Capanna |
| 6,476,603 B2 | 11/2002 | Clark et al. |
| 6,499,339 B1 | 12/2002 | Hedstrom |
| 6,515,249 B1 | 2/2003 | Valley et al. |
| 6,516,668 B2 | 2/2003 | Havira et al. |
| 6,525,658 B2 | 2/2003 | Streetman et al. |
| 6,540,180 B2 | 4/2003 | Anderson |
| 6,549,005 B1 | 4/2003 | Hay et al. |
| 6,553,838 B2 | 4/2003 | Amini |
| 6,556,945 B1 | 4/2003 | Burggraf et al. |
| 6,570,497 B2 | 5/2003 | Puckette, IV et al. |
| 6,571,636 B1 | 6/2003 | McWhorter |
| 6,588,114 B1 | 7/2003 | Daigle |
| 6,594,591 B2 | 7/2003 | Clark et al. |
| 6,600,999 B2 | 7/2003 | Clark et al. |
| 6,604,421 B1 | 8/2003 | Li |
| 6,634,112 B2 | 10/2003 | Carr et al. |
| 6,647,891 B2 | 11/2003 | Holmes et al. |
| 6,655,639 B2 | 12/2003 | Grappone |
| 6,681,160 B2 | 1/2004 | Bidaud |
| 6,715,354 B2 | 4/2004 | Wooh |
| 6,725,782 B1 | 4/2004 | Bloom et al. |
| 6,728,515 B1 | 4/2004 | Wooh |
| 6,742,392 B2 | 6/2004 | Gilmore et al. |
| 6,768,298 B2 | 7/2004 | Katragadda et al. |
| 6,778,284 B2 | 8/2004 | Casagrande |
| 6,779,761 B2 | 8/2004 | Holgate |
| 6,830,224 B2 | 12/2004 | Lewin et al. |
| 6,833,554 B2 | 12/2004 | Wooh |
| 6,845,953 B2 | 1/2005 | Hickenlooper et al. |
| 6,854,333 B2 | 2/2005 | Wooh |
| 6,895,362 B2 | 5/2005 | Davenport et al. |
| 6,945,114 B2 | 9/2005 | Cerniglia et al. |
| 6,951,132 B2 | 10/2005 | Batzinger et al. |
| 6,964,202 B2 | 11/2005 | Buttle et al. |
| 6,976,324 B2 | 12/2005 | Lichtberger et al. |
| 6,995,556 B2 | 2/2006 | Carr et al. |
| 7,007,561 B1 | 3/2006 | Conneally et al. |
| 7,023,539 B2 | 4/2006 | Kowalski |
| 7,036,232 B2 | 5/2006 | Casagrande |
| 7,036,774 B2 | 5/2006 | Hickenlooper et al. |
| 7,050,926 B2 | 5/2006 | Lichtberger et al. |
| 7,053,606 B2 | 5/2006 | Buttle et al. |
| 7,054,762 B2 | 5/2006 | Norris et al. |
| 7,081,824 B2 | 7/2006 | Gilbert |
| 7,082,881 B2 | 8/2006 | Bloom et al. |
| 7,152,330 B2 | 12/2006 | Kleeberg |
| 7,164,975 B2 | 1/2007 | Bidaud |
| 7,181,851 B2 | 2/2007 | Lichtberger et al. |
| 7,197,932 B2 | 4/2007 | Morisada et al. |
| 7,226,021 B1 | 6/2007 | Anderson et al. |
| 7,228,747 B2 | 6/2007 | Pieper |
| 7,263,886 B2 | 9/2007 | Jury |
| 7,268,565 B2 | 9/2007 | Anderson |
| 7,270,018 B2 | 9/2007 | Conneally et al. |
| 7,296,770 B2 | 11/2007 | Franke |
| 7,305,885 B2 | 12/2007 | Barshinger et al. |
| 7,311,010 B2 | 12/2007 | Otto et al. |
| 7,312,607 B2 | 12/2007 | Nygaard |
| 7,337,682 B2 | 3/2008 | Conneally et al. |
| 7,392,117 B1 | 6/2008 | Bilodeau et al. |
| 7,394,553 B2 | 7/2008 | Carr et al. |
| 7,403,296 B2 | 7/2008 | Arnold et al. |
| 7,451,632 B1 | 11/2008 | Conneally et al. |
| 7,463,348 B2 | 12/2008 | Chung |
| 7,502,670 B2 | 3/2009 | Harrison |
| 7,520,415 B2 | 4/2009 | Coomer et al. |
| 7,539,596 B2 | 5/2009 | Luke et al. |
| 7,575,201 B2 | 8/2009 | Bartonek |
| 7,616,329 B2 | 11/2009 | Nagle et al. |
| 7,659,972 B2 | 2/2010 | Magnus et al. |
| 7,698,028 B1 | 4/2010 | Bilodeau et al. |
| 7,716,010 B2 | 5/2010 | Pelletier |
| 7,752,913 B2 | 7/2010 | Brekow et al. |
| 7,755,660 B2 | 7/2010 | Carr et al. |
| 7,755,774 B2 | 7/2010 | Arnold et al. |
| 7,823,841 B2 | 11/2010 | Andarawis et al. |
| 7,849,748 B2 | 12/2010 | Havira |
| 7,869,909 B2 | 1/2011 | Harrison |
| 7,872,736 B2 | 1/2011 | Kanellopoulos et al. |
| 7,882,742 B1 | 2/2011 | Martens |
| 7,920,984 B2 | 4/2011 | Farritor |
| 7,937,246 B2 | 5/2011 | Farritor et al. |
| 7,938,370 B1 | 5/2011 | Franckart et al. |
| 7,940,389 B2 | 5/2011 | Kanellopoulos et al. |
| 7,954,770 B2 | 6/2011 | Fries et al. |
| 7,999,848 B2 | 8/2011 | Chew |
| 8,020,446 B2 | 9/2011 | Bestebreurtje |
| 8,037,763 B2 | 10/2011 | Brignac et al. |
| 8,081,320 B2 | 12/2011 | Nagle et al. |
| 8,125,219 B2 | 2/2012 | Jungbluth et al. |
| 9,108,640 B2 | 8/2015 | Jackson |
| 2001/0019263 A1 | 9/2001 | Kwun et al. |
| 2001/0045495 A1 | 11/2001 | Olson et al. |
| 2002/0065610 A1* | 5/2002 | Clark .............. B61D 15/00 702/35 |
| 2002/0113170 A1 | 8/2002 | Grappone |
| 2002/0148931 A1 | 10/2002 | Anderson |
| 2003/0020469 A1 | 1/2003 | Earnest et al. |
| 2003/0070492 A1 | 4/2003 | Buttle et al. |
| 2003/0128030 A1 | 7/2003 | Hintze et al. |
| 2004/0095135 A1 | 5/2004 | Carr et al. |
| 2004/0105608 A1 | 6/2004 | Sloman |
| 2006/0098843 A1 | 5/2006 | Chew |
| 2007/0132463 A1 | 6/2007 | Anderson |
| 2007/0145982 A1 | 6/2007 | Anderson et al. |
| 2007/0163352 A1 | 7/2007 | Bardenshtein et al. |
| 2007/0217670 A1 | 9/2007 | Bar-Am |
| 2007/0233335 A1 | 10/2007 | Kumar et al. |
| 2008/0105791 A1* | 5/2008 | Karg .............. B61K 9/10 246/120 |
| 2008/0201089 A1 | 8/2008 | Carr et al. |
| 2008/0296441 A1 | 12/2008 | Andarawis et al. |
| 2009/0132179 A1 | 5/2009 | Fu et al. |
| 2009/0266166 A1 | 10/2009 | Pagano |
| 2009/0266167 A1 | 10/2009 | Pagano |
| 2009/0282923 A1 | 11/2009 | Havira |
| 2009/0320603 A1 | 12/2009 | Crocker et al. |
| 2010/0207620 A1 | 8/2010 | Gies |
| 2010/0312493 A1 | 12/2010 | Chen et al. |
| 2011/0006167 A1 | 1/2011 | Tolmei |
| 2011/0043199 A1 | 2/2011 | Crocker |
| 2011/0199607 A1 | 8/2011 | Kanellopoulos et al. |
| 2011/0216996 A1 | 9/2011 | Rogers |
| 2011/0233293 A1 | 9/2011 | Kral et al. |
| 2011/0255077 A1 | 10/2011 | Rogers |
| 2011/0276203 A1 | 11/2011 | Hase |

FOREIGN PATENT DOCUMENTS

| | | |
|---|---|---|
| WO | 0009377 | 2/2000 |
| WO | 0230729 | 4/2002 |
| WO | 02060738 | 8/2002 |
| WO | 2007110613 | 10/2007 |
| WO | 2008012535 | 1/2008 |
| WO | 2008099177 | 8/2008 |

(56) References Cited

FOREIGN PATENT DOCUMENTS

| WO | 2009087385 | 7/2009 |
|----|------------|--------|
| WO | 2011146088 | 11/2011 |

OTHER PUBLICATIONS

Aharoni, R.; Glikman, Eli; "A Novel high-speed rail inspection system", ScanMaster Systems (IRT) Ltd., Oct. 2002, vol. 7, No. 10, 8 pgs.
http://www.progressiverailroading.com/mow/article/Maintenance-of-Way-Track-inspection, "Maintenance of Way: Track inspection technology", 7 pgs.
Rose, J.L.; Avioli, M.J.; Song, W.J., "Application and potential of guided wave rail inspection", Insight vol. 44, No. 6., Jun. 2002, 6 pgs.
Sperry Rail Service, Sperry B-Scan Dual Rail Inspection System, For superior technology, training, and reporting, the solution is Sperry, 4 pgs.
Hocking, Rail Inspection, The Eddy Current Solution, 17 pgs.
Innotrack, Project No. TIP5-CT-2006-031415, 43 pgs.

* cited by examiner

ROUTE EXAMINING SYSTEM AND METHOD

CROSS-REFERENCE TO RELATED APPLICATIONS

This application is a continuation of International Application No. PCT/US13/54284, which was filed on 9 Aug. 2013, and is entitled "Route Examining System and Method". International Application No. PCT/US13/54284 claims priority to U.S. Provisional Application No. 61/681,843, which was filed on 10 Aug. 2012 and is entitled "Adaptive Energy Transfer System And Method", U.S. Provisional Application Ser. No. 61/729,188, which was filed on 21 Nov. 2012 and is entitled "Route Examining System And Method," U.S. Provisional Application Ser. No. 61/860,469, which was filed on 31 Jul. 2013 and is entitled "Route Examining System And Method," and U.S. Provisional Application Ser. No. 61/860,496, which was filed on 31 Jul. 2013 and is entitled "Route Examining System And Method," all of which aforementioned provisional applications are hereby incorporated by reference herein in their entireties.

TECHNICAL FIELD

Embodiments of the subject matter disclosed herein relate to examining routes traveled by vehicles for damage to the routes, and more particularly to mitigation of damaged or dangerous portions of routes determined during examination of the routes.

BACKGROUND

Routes that are traveled by vehicles may become damaged over time with extended use. For example, tracks on which rail vehicles travel may become damaged and/or broken. A variety of known systems are used to examine rail tracks to identify where the damaged and/or broken portions of the track are located. For example, some systems use cameras, lasers, and the like, to optically detect breaks and damage to the tracks. The cameras and lasers may be mounted on the rail vehicles, but the accuracy of the cameras and lasers may be limited by the speed at which the rail vehicles move during inspection of the route. As a result, the cameras and lasers may not be able to be used during regular operation (e.g., travel) of the rail vehicles in revenue service.

Other systems use ultrasonic transducers that are placed at or near the tracks to ultrasonically inspect the tracks. These systems may require very slow movement of the transducers relative to the tracks in order to detect damage to the track. When a suspect location is found by an ultrasonic inspection vehicle, a follow-up manual inspection may be required for confirmation of defects using transducers that are manually positioned and moved along the track and/or are moved along the track by a relatively slower moving inspection vehicle. Inspections of the track can take a considerable amount of time, during which the inspected section of the route may be unusable by regular route traffic.

Other systems use wayside devices that send electric signals through the tracks. If the signals are not received by other wayside devices, then a circuit that includes the track is identified as being open and the track is considered to be broken. These systems are limited at least in that the wayside devices are immobile. As a result, the systems cannot inspect large spans of track and/or a large number of devices must be installed in order to inspect the large spans of track.

Other systems use human inspectors who move along the track to inspect for broken and/or damaged sections of track. This manual inspection is slow and prone to errors.

BRIEF DESCRIPTION

In an embodiment, a system (e.g., a route examination system) includes at least one examining module configured to be disposed onboard a vehicle system and a mitigation module. The at least one examining module is configured to identify an identified section of a route being traversed by the vehicle system, with the identified section corresponding to at least one of a potentially damaged section of the route or an actually damaged section of the route. The at least one examining module includes an application device configured to be disposed onboard the vehicle system and to be at least one of conductively or inductively coupled with the route during travel along the route. The at least one examining module also includes a detection unit configured to monitor one or more electrical characteristics of the route in response to an examination signal injected into the route by the application device. Also, the at least one examining module includes an identification unit configured to examine the one or more electrical characteristics of the route in order to determine whether a section of the route extending between the application device and the detection unit is potentially damaged based on the one or more electrical characteristics. The mitigation module is configured to, responsive to an identification by the at least one examining module of the identified section of the route, automatically perform a mitigation action corresponding to the identified section of the route.

In an embodiment, a method includes electrically injecting an examination signal into a route being traveled by a vehicle system. The examination signal is injected into the route by the vehicle system. The method also includes monitoring one or more electrical characteristics of the route responsive to the examination signal. Also, the method includes identifying, with an identification unit, a potentially damaged section of the route based on the one or more electrical characteristics. Further, the method includes performing, automatically, with a mitigation module, responsive to an identification of the potentially damaged section of the route by the identification unit, a mitigation action corresponding to the identified section of the route.

In an embodiment, a tangible and non-transitory computer readable medium comprising one or more computer software modules configured to direct one or more processors to control electrical injection of an examination signal into a route being traveled by a vehicle system, the examination signal being injected into the route by the vehicle system. The one or more computer software modules are also configured to direct the one or more processors to monitor one or more electrical characteristics of the route responsive to the examination signal. The one or more computer software modules are also configured to direct the one or more processors to identify a potentially damaged section of the route based on the one or more electrical characteristics. The one or more computer software modules are also configured to direct the one or more processors to perform, responsive to an identification of the potentially damaged section of the route, a mitigation action corresponding to the identified section of the route.

BRIEF DESCRIPTION OF THE DRAWINGS

Reference is made to the accompanying drawings in which particular embodiments and further benefits of the invention are illustrated as described in more detail in the description below, in which.

DETAILED DESCRIPTION

Figure 1:
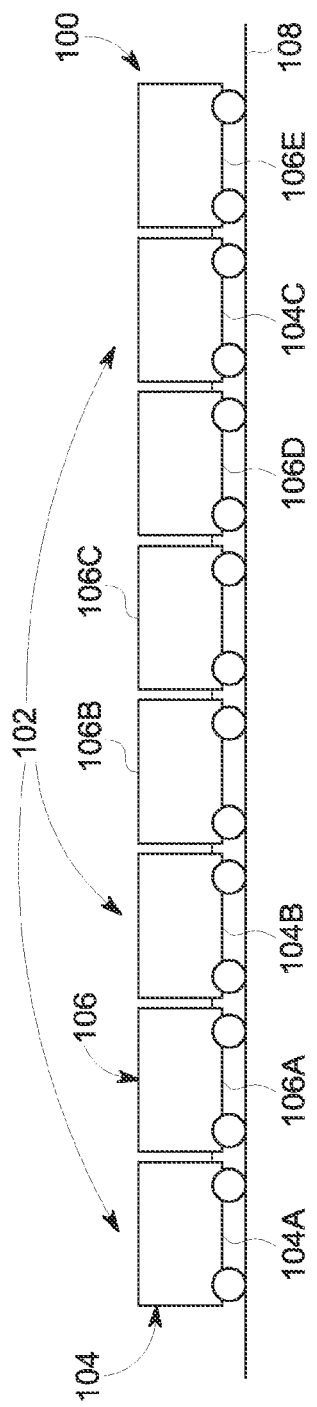
FIG. 1 is a schematic illustration of a vehicle system that includes an embodiment of a route examining system.

Embodiments of the inventive subject matter relate to methods and systems for examining a route being traveled upon by a vehicle system in order to identify potential sections of the route that are damaged or broken, and for automatically performing one or more mitigating or corrective actions responsive to the examination of the route. As used herein, a mitigating action may include one or more of reducing a risk or expense of traversing the route, repairing the route, replacing a portion of the route, or increasing monitoring of a route. In various embodiments, for example, the vehicle system may examine the route by injecting an examination signal into the route and monitoring one or more electrical characteristics of the route as the examination signal is transmitted through the route to identify one or more potential sections of the route that are potentially damaged (e.g., one or more sections having a broken or partially broken rail). Additionally or alternatively, other route examination techniques may be employed. The vehicle system may then automatically implement one or more mitigation activities based on the examination of the route.

In various embodiments, upon detection of an alarm condition (e.g., a potentially or actually damaged section of track), one or mitigation activities may be automatically implemented, for example via a mitigation module disposed onboard a vehicle traveling a route. It may be noted that in various embodiments, the mitigation module may be disposed off-board a vehicle.

In various embodiments, an alarm (with or without an accompanying message) may be displayed to an operator of a vehicle system to take a standard action (e.g., slow down below a threshold speed for any alarm) and/or to take an action tailored for a given set of circumstances (e.g., a particular speed based on vehicle size and configuration, curvature and/or grade of the route, or extent or type of damage, among others). In various embodiments, the alarm (and/or a subsequent confirmation of the alarm condition) may automatically trigger autonomous control actions of one or more vehicle systems. As just one example, a detection of a broken rail may cause an associated system, such as a trip planning and vehicle control system, to close a throttle to an "idle" setting and apply a minimum brake pipe reduction to keep a vehicle system stretched as the vehicle comes to a stop. Such action, for example, may minimize the risk of derailment and/or minimize the severity of consequences if a derailment occurs. In some embodiments, the alarm condition may be broadcast to other vehicles (directly and/or indirectly via a scheduling or dispatch center). For example, vehicles traveling an adjacent route may be slowed or stopped to minimize risk of the vehicles on the adjacent track colliding with a derailment caused by the identified damage, and/or as a precaution in case the cause of damage to the track has also damaged one or more adjacent tracks. Further still, in various embodiments, mitigation actions may be linked to trip planners of additional vehicles, movement planners or scheduling planners of a dispatch center, wayside stations (e.g., crossing control, switch control), and/or positive train control (PTC) systems, for example, to prevent travel over an identified section, to reduce travel over an identified section, to slow travel over an identified section, and/or to re-route travel away from the identified section.

In various embodiments, the route may be a track of a rail vehicle system and the vehicle system may be configured to identify a potentially broken or partially broken section of one or more rails of the track. The electrical signal that is injected into the route may be powered by an onboard energy storage device, such as one or more batteries, and/or an off-board energy source, such as a catenary and/or electrified rail of the route.

A technical effect of at least one embodiment includes improved safety of a transportation network. A technical effect of at least one embodiment includes improved quality of response to an identification of breaks or other damage along a route. A technical effect of at least one embodiment includes improved efficiency of allocation of maintenance and/or inspection resources. A technical effect of at least one embodiment includes reducing time elapsed before mitigation activity is directed to an identified potentially damaged section of a route. A technical effect of at least one embodiment includes elimination of delay of implementation and/or mis-interpretation of a mitigation command to an operator.

The term "vehicle" as used herein can be defined as a mobile machine that transports at least one of a person, people, or a cargo. For instance, a vehicle can be, but is not limited to being, a rail car, an intermodal container, a locomotive, a marine vessel, mining equipment, construction equipment, an automobile, and the like. A "vehicle system" includes two or more vehicles that are interconnected with each other to travel along a route. For example, a vehicle system can include two or more vehicles that are directly connected to each other (e.g., by a coupler) or that are indirectly connected with each other (e.g., by one or more other vehicles and couplers). A vehicle system can be referred to as a consist, such as a rail vehicle consist.

"Software" or "computer program" as used herein includes, but is not limited to, one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, an application, instructions stored in a memory, part of an operating system or other type of executable instructions. "Computer" or "processing element" or "computer device" as used herein includes, but is not limited to, any programmed or programmable electronic device that can store, retrieve, and process data. "Non-transitory computer-readable media" include, but are not limited to, a CD-ROM, a removable flash memory card, a hard disk drive, a magnetic tape, and a floppy disk. "Computer memory", as used herein, refers to a storage device configured to store digital data or information which can be retrieved by a computer or processing element. "Controller," "unit," and/or "module," as used herein, can to the logic circuitry and/or processing elements and associated software or program involved in controlling an energy storage system. The terms "signal", "data", and "information" may be used interchangeably herein and may refer to digital or analog forms.

FIG. 1 is a schematic illustration of a vehicle system 100 that includes an embodiment of a route examining system 102. The vehicle system 100 includes several vehicles 104, 106 that are mechanically connected with each other to travel along a route 108. The vehicles 104 (e.g., the vehicles 104A-C) represent propulsion-generating vehicles, such as vehicles that generate tractive effort or power in order to propel the vehicle system 100 along the route 108. In an embodiment, the vehicles 104 can represent rail vehicles such as locomotives. The vehicles 106 (e.g., the vehicles 106A-E) represent non-propulsion generating vehicles, such as vehicles that do not generate tractive effort or power. In an embodiment, the vehicles 106 can represent rail cars. Alternatively, the vehicles 104, 106 may represent other types of vehicles. In another embodiment, one or more of the individual vehicles 104 and/or 106 represent a group of vehicles, such as a consist of locomotives or other vehicles.

The route 108 can be a body, surface, or medium on which the vehicle system 100 travels. In an embodiment, the route 108 can include or represent a body that is capable of conveying a signal between vehicles in the vehicle system 100, such as a conductive body capable of conveying an electrical signal (e.g., a direct current, alternating current, radio frequency, or other signal).

The examining system 102 can be distributed between or among two or more vehicles 104, 106 of the vehicle system 100. For example, the examining system 102 may include two or more components that operate to identify potentially damaged sections of the route 108, with at least one component disposed on each of two different vehicles 104, 106 in the same vehicle system 100. Returning to FIG. 1, in the illustrated embodiment, the examining system 102 is distributed between or among two different vehicles 104. Alternatively, the examining system 102 may be distributed among three or more vehicles 104, 106. Additionally or alternatively, the examining system 102 may be distributed between one or more vehicles 104 and one or more vehicles 106, and is not limited to being disposed onboard a single type of vehicle 104 or 106. As described below, in another embodiment, the examining system 102 may be distributed between a vehicle in the vehicle system and an off-board monitoring location, such as a wayside device.

In operation, the vehicle system 100 travels along the route 108. A first vehicle 104 electrically injects an examination signal into the route 108. For example, the first vehicle 104A may apply a direct current, alternating current, radio frequency signal, or the like, to the route 108 as an examination signal. The examination signal propagates through or along the route 108. A second vehicle 104B or 104C may monitor one or more electrical characteristics of the route 108 when the examination signal is injected into the route 108.

The examining system 102 can be distributed among two separate vehicles 104 and/or 106. In the illustrated embodiment, the examining system 102 has components disposed onboard at least two of the propulsion-generating vehicles 104A, 104B, 104C. Additionally or alternatively, the examining system 102 may include components disposed onboard at least one of the non-propulsion generating vehicles 106. For example, the examining system 102 may be located onboard two or more propulsion-generating vehicles 104, two or more non-propulsion generating vehicles 106, or at least one propulsion-generating vehicle 104 and at least one non-propulsion generating vehicle 106.

In operation, during travel of the vehicle system 100 along the route 108, the examining system 102 electrically injects an examination signal into the route 108 at a first vehicle 104 or 106 (e.g., beneath the footprint of the first vehicle 104 or 106). For example, an onboard or off-board power source may be controlled to apply a direct current, alternating current, RF signal, or the like, to a track of the route 108. The examining system 102 monitors electrical characteristics of the route 108 at a second vehicle 104 or 106 of the same vehicle system 100 (e.g., beneath the footprint of the second vehicle 104 or 106) in order to determine if the examination signal is detected in the route 108. For example, the voltage, current, resistance, impedance, or other electrical characteristic of the route 108 may be monitored at the second vehicle 104, 106 in order to determine if the examination signal is detected and/or if the examination signal has been altered. If the portion of the route 108 between the first and second vehicles conducts the examination signal to the second vehicle, then the examination signal may be detected by the examining system 102. The examining system 102 may determine that the route 108 (e.g., the portion of the route 108 through which the examination signal propagated) is intact and/or not damaged.

On the other hand, if the portion of the route 108 between the first and second vehicles does not conduct the examination signal to the second vehicle (e.g., such that the examination signal is not detected in the route 108 at the second vehicle), then the examination signal may not be detected by the examining system 102. The examining system 102 may determine that the route 108 (e.g., the portion of the route 108 disposed between the first and second vehicles during the time period that the examination signal is expected or calculated to propagate through the route 108) is not intact and/or is damaged. For example, the examining system 102 may determine that the portion of a track between the first and second vehicles is broken such that a continuous conductive pathway for propagation of the examination signal does not exist. The examining system 102 can identify this section of the route as being a potentially damaged section of the route 108. In routes 108 that are segmented (e.g., such as rail tracks that may have gaps), the examining system 102 may transmit and attempt to detect multiple examination signals in order to prevent false detection of a broken portion of the route 108.

Because the examination signal may propagate relatively quickly through the route 108 (e.g., faster than a speed at which the vehicle system 100 moves), the route 108 can be examined using the examination signal when the vehicle system 100 is moving, such as transporting cargo or otherwise operating at or above a non-zero, minimum speed limit of the route 108.

Additionally or alternatively, the examining system 102 may detect one or more changes in the examination signal at the second vehicle. The examination signal may propagate through the route 108 from the first vehicle to the second vehicle. But, due to damaged portions of the route 108 between the first and second vehicles, one or more signal characteristics of the examination signal may have changed. For example, the signal-to-noise ratio, intensity, power, or the like, of the examination signal may be known or designated when injected into the route 108 at the first vehicle. One or more of these signal characteristics may change (e.g., deteriorate or decrease) during propagation through a mechanically damaged or deteriorated portion of the route 108, even though the examination signal is received (e.g., detected) at the second vehicle. The signal characteristics can be monitored upon receipt of the examination signal at the second vehicle. Based on changes in one or more of the signal characteristics, the examining system 102 may identify the portion of the route 108 that is disposed between the first and second vehicles as being a potentially damaged portion of the route 108. For example, if the signal-to-noise ratio, intensity, power, or the like, of the examination signal decreases below a designated threshold and/or decreases by more than a designated threshold decrease, then the examining system 102 may identify the section of the route 108 as being potentially damaged.

In response to identifying a section of the route 108 as being damaged or potentially damaged, the examining system 102 may initiate one or more responsive actions. For example, the examining system 102 can automatically slow down or stop movement of the vehicle system 100. The examining system 102 can automatically issue a warning signal to one or more other vehicle systems traveling nearby of the potentially damaged section of the route 108 and where the potentially damaged section of the route 108 is located. The examining system 102 may automatically communicate a warning signal to a stationary wayside device located at or near the route 108 that notifies the device of the potentially damaged section of the route 108 and the location of the potentially damaged section. The stationary wayside device can then communicate a signal to one or more other vehicle systems traveling nearby of the potentially damaged section of the route 108 and where the potentially damaged section of the route 108 is located. The examining system 102 may automatically issue an inspection signal to an off-board facility, such as a repair facility, that notifies the facility of the potentially damaged section of the route 108 and the location of the section. The facility may then send one or more inspectors to check and/or repair the route 108 at the potentially damaged section. Alternatively, the examining system 102 may notify an operator of the potentially damaged section of the route 108 and the operator may then manually initiate one or more responsive actions.

Figure 2:
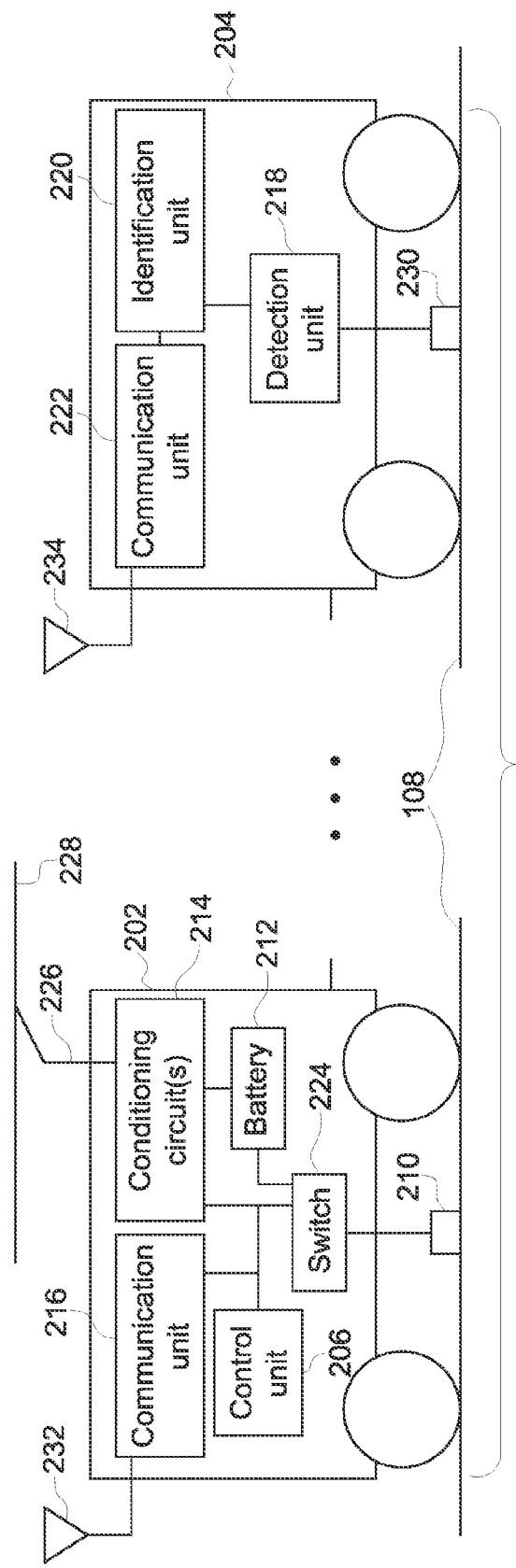
FIG. 2 is a schematic illustration of an embodiment of an examining system.

FIG. 2 is a schematic illustration of an embodiment of an examining system 200. The examining system 200 may represent the examining system 102 shown in FIG. 1. The examining system 200 is distributed between a first vehicle 202 and a second vehicle 204 in the same vehicle system. The vehicles 202, 204 may represent vehicles 104 and/or 106 of the vehicle system 100 shown in FIG. 1. In an embodiment, the vehicles 202, 204 represent two of the vehicles 104, such as the vehicle 104A and the vehicle 104B, the vehicle 104B and the vehicle 104C, or the vehicle 104A and the vehicle 104C. Alternatively, one or more of the vehicles 202, 204 may represent at least one of the vehicles 106. In another embodiment, the examining system 200 may be distributed among three or more of the vehicles 104 and/or 106.

The examining system 200 includes several components described below that are disposed onboard the vehicles 202, 204. For example, the illustrated embodiment of the examining system 200 includes a control unit 208, an application device 210, an onboard power source 212 ("Battery" in FIG. 2), one or more conditioning circuits 214, a communication unit 216, and one or more switches 224 disposed onboard the first vehicle 202. The examining system 200 also includes a detection unit 218, an identification unit 220, a detection device 230, and a communication unit 222 disposed onboard the second vehicle 204. Alternatively, one or more of the control unit 208, application device 210, power source 212, conditioning circuits 214, communication unit 216, and/or switch 224 may be disposed onboard the second vehicle 204 and/or another vehicle in the same vehicle system, and/or one or more of the detection unit 218, identification unit 220, detection device 230, and communication unit 222 may be disposed onboard the first vehicle 202 and/or another vehicle in the same vehicle system.

The control unit 206 controls supply of electric current to the application device 210. In an embodiment, the application device 210 includes one or more conductive bodies that engage the route 108 as the vehicle system that includes the vehicle 202 travels along the route 108. For example, the application device 210 can include a conductive shoe, brush, or other body that slides along an upper and/or side surface of a track such that a conductive pathway is created that extends through the application device 210 and the track. Additionally or alternatively, the application device 210 can include a conductive portion of a wheel of the first vehicle 202, such as the conductive outer periphery or circumference of the wheel that engages the route 108 as the first vehicle 202 travels along the route 108. In another embodiment, the application device 210 may be inductively coupled with the route 108 without engaging or touching the route 108 or any component that engages the route 108.

The application device 210 is conductively coupled with the switch 224, which can represent one or more devices that control the flow of electric current from the onboard power source 212 and/or the conditioning circuits 214. The switch 224 can be controlled by the control unit 206 so that the control unit 206 can turn on or off the flow of electric current through the application device 210 to the route 108. In an embodiment, the switch 224 also can be controlled by the control unit 206 to vary one or more waveforms and/or waveform characteristics (e.g., phase, frequency, amplitude, and the like) of the current that is applied to the route 108 by the application device 210.

The onboard power source 212 represents one or more devices capable of storing electric energy, such as one or more batteries, capacitors, flywheels, and the like. Additionally or alternatively, the power source 212 may represent one or more devices capable of generating electric current, such as an alternator, generator, photovoltaic device, gas turbine, or the like. The power source 212 is coupled with the switch 224 so that the control unit 206 can control when the electric energy stored in the power source 212 and/or the electric current generated by the power source 212 is conveyed as electric current (e.g., direct current, alternating current, an RF signal, or the like) to the route 108 via the application device 210.

The conditioning circuit 214 represents one or more circuits and electric components that change characteristics of electric current. For example, the conditioning circuit 214 may include one or more inverters, converters, transformers, batteries, capacitors, resistors, inductors, and the like. In the illustrated embodiment, the conditioning circuit 214 is coupled with a connecting assembly 226 that is configured to receive electric current from an off-board source. For example, the connecting assembly 226 may include a pantograph that engages an electrified conductive pathway 228 (e.g., a catenary) extending along the route 108 such that the electric current from the catenary 228 is conveyed via the connecting assembly 226 to the conditioning circuit 214. Additionally or alternatively, the electrified conductive pathway 228 may represent an electrified portion of the route 108 (e.g., an electrified rail) and the connecting assembly 226 may include a conductive shoe, brush, portion of a wheel, or other body that engages the electrified portion of the route 108. Electric current is conveyed from the electrified portion of the route 108 through the connecting assembly 226 and to the conditioning circuit 214.

The electric current that is conveyed to the conditioning circuit 214 from the power source 212 and/or the off-board source (e.g., via the connecting assembly 226) can be altered by the conditioning circuit 214. For example, the conditioning circuit 214 can change the voltage, current, frequency, phase, magnitude, intensity, waveform, and the like, of the current that is received from the power source 212 and/or the connecting assembly 226. The modified current can be the examination signal that is electrically injected into the route 108 by the application device 210. Additionally or alternatively, the control unit 206 can form the examination signal by controlling the switch 224. For example, the examination signal can be formed by turning the switch 224 on to allow current to flow from the conditioning circuit 214 and/or the power source 212 to the application device 210.

In an embodiment, the control unit 206 may control the conditioning circuit 214 to form the examination signal. For example, the control unit 206 may control the conditioning circuit 214 to change the voltage, current, frequency, phase, magnitude, intensity, waveform, and the like, of the current that is received from the power source 212 and/or the connecting assembly 226 to form the examination signal.

The examination signal is conducted through the application device 210 to the route 108, and is electrically injected into a conductive portion of the route 108. For example, the examination signal may be conducted into a conductive track of the route 108. In another embodiment, the application device 210 may not directly engage (e.g., touch) the route 108, but may be wirelessly coupled with the route 108 in order to electrically inject the examination signal into the route 108 (e.g., via induction).

The conductive portion of the route 108 that extends between the first and second vehicles 202, 204 during travel of the vehicle system may form a track circuit through which the examination signal may be conducted. The first vehicle 202 can be coupled (e.g., coupled physically, coupled wirelessly, among others) to the track circuit by the application device 210. The power source (e.g., the onboard power source 212 and/or the off-board electrified conductive pathway 228) can transfer power (e.g., the examination signal) through the track circuit toward the second vehicle 204.

By way of example and not limitation, the first vehicle 202 can be coupled to a track of the route 108, and the track can be the track circuit that extends and conductively couples one or more components of the examining system 200 on the first vehicle 202 with one or more components of the examining system 200 on the second vehicle 204.

In an embodiment, the control unit 206 includes or represents the manager component described in the '843 Application. For example, the control unit 206 may represent the manager component 210 in the '843 Application. Such a manager component can be configured to activate a transmission of electric current into the route 108 via the application device 210. In another instance, the manager component can activate or deactivate a transfer of the portion of power from the onboard and/or off-board power source to the application device 210, such as by controlling the switch and/or conditioning circuit. Moreover, the manager component can adjust parameter(s) associated with the portion of power that is transferred to the route 108. For instance, the manager component can adjust an amount of power transferred, a frequency at which the power is transferred (e.g., a pulsed power delivery, AC power, among others), a duration of time the portion of power is transferred, among others. Such parameter(s) can be adjusted by the manager component based on at least one of a geographic location of the vehicle or the device or an identification of the device (e.g., type, location, make, model, among others).

The manager component can leverage a geographic location of the vehicle or the device in order to adjust a parameter for the portion of power that can be transferred to the device from the power source. For instance, the amount of power transferred can be adjusted by the manager component based on the device power input. By way of example and not limitation, the portion of power transferred can meet or be below the device power input in order to reduce risk of damage to the device. In another example, the geographic location of the vehicle and/or the device can be utilized to identify a particular device and, in turn, a power input for such device. The geographic location of the vehicle and/or the device can be ascertained by a location on a track circuit, identification of the track circuit, Global Positioning Service (GPS), among others.

The detection unit 218 disposed onboard the second vehicle 204 as shown in FIG. 2 monitors the route 108 to attempt to detect the examination signal that is injected into the route 108 by the first vehicle 202. The detection unit 218 is coupled with the detection device 230. In an embodiment, the detection device 230 includes one or more conductive bodies that engage the route 108 as the vehicle system that includes the vehicle 204 travels along the route 108. For example, the detection device 230 can include a conductive shoe, brush, or other body that slides along an upper and/or side surface of a track such that a conductive pathway is created that extends through the detection device 230 and the track. Additionally or alternatively, the detection device 230 can include a conductive portion of a wheel of the second vehicle 204, such as the conductive outer periphery or circumference of the wheel that engages the route 108 as the second vehicle 204 travels along the route 108. In another embodiment, the detection device 230 may be inductively coupled with the route 108 without engaging or touching the route 108 or any component that engages the route 108.

The detection unit 218 monitors one or more electrical characteristics of the route 108 using the detection device 230. For example, the voltage of a direct current conducted by the route 108 may be detected by monitoring the voltage conducted by from the route 108 to the detection device 230 and/or the current (e.g., frequency, amps, phases, or the like) of an alternating current or RF signal being conducted by the route 108 may be detected by monitoring the current conducted by the route 108 to the detection device 230. As another example, the signal-to-noise ratio of a signal being conducted by the detection device 230 from the route 108 may be detected by the detection unit 218 examining the signal conducted by the detection device 230 (e.g., a received signal) and comparing the received signal to a designated signal. For example, the examination signal that is injected into the route 108 using the application device 210 may include a designated signal or portion of a designated signal. The detection unit 218 may compare the received signal that is conducted from the route 108 into the detection device 230 with this designated signal in order to measure a signal-to-noise ratio of the received signal.

The detection unit 218 determines one or more electrical characteristics of the signal (e.g., voltage, frequency, phase, waveform, intensity, or the like) that is received (e.g., picked up) by the detection device 230 from the route 108 and reports the characteristics of the received signal to the identification unit 220. If no signal is received by the detection device 230, then the detection unit 218 may report the absence of such a signal to the identification unit 220. For example, if the detection unit 218 does not detect at least a designated voltage, designated current, or the like, as being received by the detection device 230, then the detection unit 218 may not detect any received signal. Alternatively or additionally, the detection unit 218 may communicate the detection of a signal that is received by the detection device 230 only upon detection of the signal by the detection device 230.

In an embodiment, the detection unit 218 may determine the characteristics of the signals received by the detection device 230 in response to a notification received from the control unit 206 in the first vehicle 202. For example, when the control unit 206 is to cause the application device 210 to inject the examination signal into the route 108, the control unit 206 may direct the communication unit 216 to transmit a notification signal to the detection device 230 via the communication unit 222 of the second vehicle 204. The communication units 216, 222 may include respective antennas 232, 234 and associated circuitry for wirelessly communicating signals between the vehicles 202, 204, and/or with off-board locations. The communication unit 216 may wirelessly transmit a notification to the detection unit 218 that instructs the detection unit 218 as to when the examination signal is to be input into the route 108. Additionally or alternatively, the communication units 216, 222 may be connected via one or more wires, cables, and the like, such as a multiple unit (MU) cable, trainline, or other conductive pathway(s), to allow communication between the communication units 216, 222.

The detection unit 218 may begin monitoring signals received by the detection device 230. For example, the detection unit 218 may not begin or resume monitoring the received signals of the detection device 230 unless or until the detection unit 218 is instructed that the control unit 206 is causing the injection of the examination signal into the route 108. Alternatively or additionally, the detection unit 218 may periodically monitor the detection device 230 for received signals and/or may monitor the detection device 230 for received signals upon being manually prompted by an operator of the examining system 200.

The identification unit 220 receives the characteristics of the received signal from the detection unit 218 and determines if the characteristics indicate receipt of all or a portion of the examination signal injected into the route 108 by the first vehicle 202. Although the detection unit 218 and the identification unit 220 are shown as separate units, the detection unit 218 and the identification unit 220 may refer to the same unit. For example, the detection unit 218 and the identification unit 220 may be a single hardware component disposed onboard the second vehicle 204.

The identification unit 220 examines the characteristics and determines if the characteristics indicate that the section of the route 108 disposed between the first vehicle 202 and the second vehicle 204 is damaged or at least partially damaged. For example, if the application device 210 injected the examination signal into a track of the route 108 and one or more characteristics (e.g., voltage, current, frequency, intensity, signal-to-noise ratio, and the like) of the examination signal are not detected by the detection unit 218, then, the identification unit 220 may determine that the section of the track that was disposed between the vehicles 202, 204 is broken or otherwise damaged such that the track cannot conduct the examination signal. Additionally or alternatively, the identification unit 220 can examine the signal-to-noise ratio of the signal detected by the detection unit 218 and determine if the section of the route 108 between the vehicles 202, 204 is potentially broken or damaged. For example, the identification unit 220 may identify this section of the route 108 as being broken or damaged if the signal-to-noise ratio of one or more (or at least a designated amount) of the received signals is less than a designated ratio.

The identification unit 220 may include or be communicatively coupled (e.g., by one or more wired and/or wireless connections that allow communication) with a location determining unit that can determine the location of the vehicle 204 and/or vehicle system. For example, the location determining unit may include a GPS unit or other device that can determine where the first vehicle and/or second vehicle are located along the route 108. The distance between the first vehicle 202 and the second vehicle 204 along the length of the vehicle system may be known to the identification unit 220, such as by inputting the distance into the identification unit 220 using one or more input devices and/or via the communication unit 222.

The identification unit 220 can identify which section of the route 108 is potentially damaged based on the location of the first vehicle 202 and/or the second vehicle 204 during transmission of the examination signal through the route 108. For example, the identification unit 220 can identify the section of the route 108 that is within a designated distance of the vehicle system, the first vehicle 202, and/or the second vehicle 204 as the potentially damaged section when the identification unit 220 determines that the examination signal is not received or has a decreased signal-to-noise ratio.

Additionally or alternatively, the identification unit 220 can identify which section of the route 108 is potentially damaged based on the locations of the first vehicle 202 and the second vehicle 204 during transmission of the examination signal through the route 108, the direction of travel of the vehicle system that includes the vehicles 202, 204, the speed of the vehicle system, and/or a speed of propagation of the examination signal through the route 108. The speed of propagation of the examination signal may be a designated speed that is based on one or more of the material(s) from which the route 108 is formed, the type of examination signal that is injected into the route 108, and the like. In an embodiment, the identification unit 220 may be notified when the examination signal is injected into the route 108 via the notification provided by the control unit 206. The identification unit 220 can then determine which portion of the route 108 is disposed between the first vehicle 202 and the second vehicle 204 as the vehicle system moves along the route 108 during the time period that corresponds to when the examination signal is expected to be propagating through the route 108 between the vehicles 202, 204 as the vehicles 202, 204 move. This portion of the route 108 may be the section of potentially damaged route that is identified.

One or more responsive actions may be initiated when the potentially damaged section of the route 108 is identified. For example, in response to identifying the potentially damaged portion of the route 108, the identification unit 220 may notify the control unit 206 via the communication units 222, 216. The control unit 206 and/or the identification unit 220 can automatically slow down or stop movement of the vehicle system. For example, the control unit 206 and/or identification unit 220 can be communicatively coupled with one or more propulsion systems (e.g., engines, alternators/generators, motors, and the like) of one or more of the propulsion-generating vehicles in the vehicle system. The control unit 206 and/or identification unit 220 may automatically direct the propulsion systems to slow down and/or stop.

Figure 3:
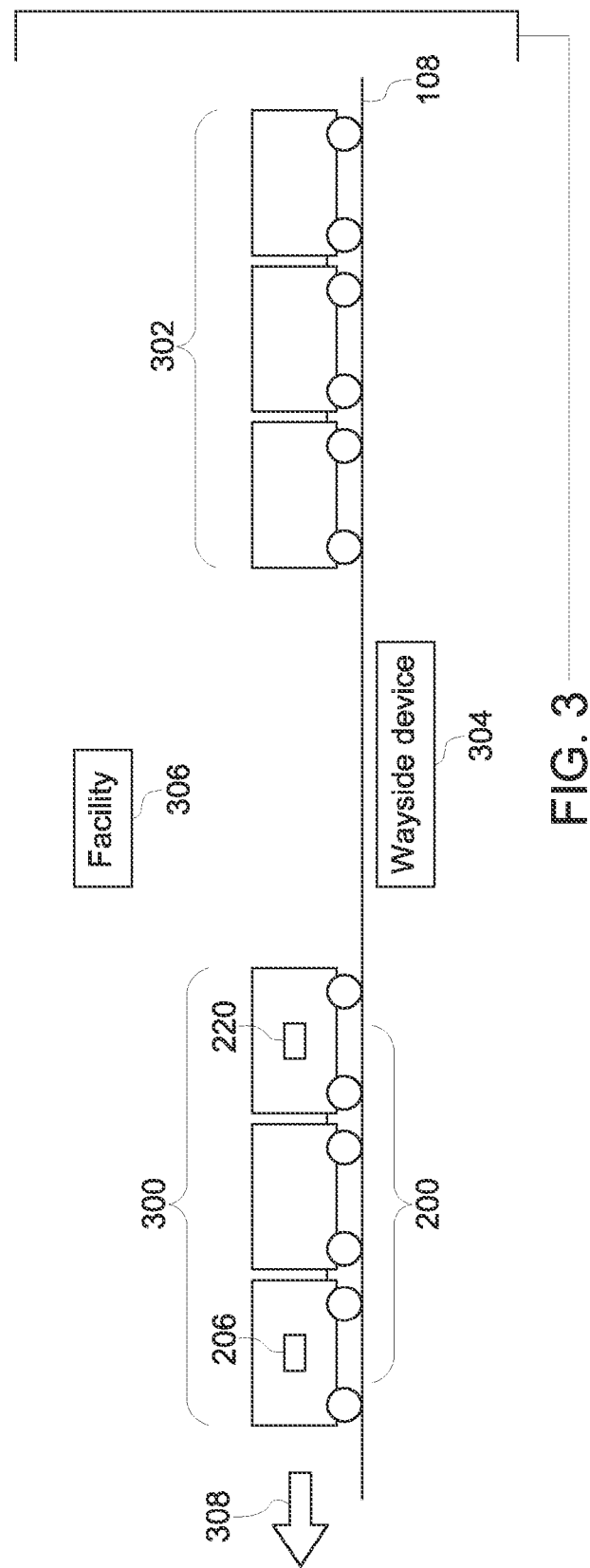
FIG. 3 illustrates a schematic diagram of an embodiment of plural vehicle systems traveling along the route.

With continued reference to FIG. 2, FIG. 3 illustrates a schematic diagram of an embodiment of plural vehicle systems 300, 302 traveling along the route 108. One or more of the vehicle systems 300, 302 may represent the vehicle system 100 shown in FIG. 1 that includes the route examining system 200. For example, at least a first vehicle system 300 traveling along the route 108 in a first direction 308 may include the examining system 200. The second vehicle system 302 may be following the first vehicle system 300 on the route 108, but spaced apart and separated from the first vehicle system 300.

In addition or as an alternate to the responsive actions that may be taken when a potentially damaged section of the route 108 is identified, the examining system 200 onboard the first vehicle system 300 may automatically notify the second vehicle system 302. The control unit 206 and/or the identification unit 220 may wirelessly communicate (e.g., transmit or broadcast) a warning signal to the second vehicle system 302. The warning signal may notify the second vehicle system 302 of the location of the potentially damaged section of the route 108 before the second vehicle system 302 arrives at the potentially damaged section. The second vehicle system 302 may be able to slow down, stop, or move to another route to avoid traveling over the potentially damaged section.

Additionally or alternatively, the control unit 206 and/or identification unit 220 may communicate a warning signal to a stationary wayside device 304 in response to identifying a section of the route 108 as being potentially damaged. The device 304 can be, for instance, wayside equipment, an electrical device, a client asset, a defect detection device, a device utilized with Positive Train Control (PTC), a signal system component(s), a device utilized with Automated Equipment Identification (AEI), among others. In one example, the device 304 can be a device utilized with AEI. AEI is an automated equipment identification mechanism that can aggregate data related to equipment for the vehicle. By way of example and not limitation, AEI can utilize passive radio frequency technology in which a tag (e.g., passive tag) is associated with the vehicle and a reader/receiver receives data from the tag when in geographic proximity thereto. The AEI device can be a reader or receiver that collects or stores data from a passive tag, a data store that stores data related to passive tag information received from a vehicle, an antenna that facilitates communication between the vehicle and a passive tag, among others. Such an AEI device may store an indication of where the potentially damaged section of the route 108 is located so that the second vehicle system 302 may obtain this indication when the second vehicle system 302 reads information from the AEI device.

In another example, the device 304 can be a signaling device for the vehicle. For instance, the device 304 can provide visual and/or audible warnings to provide warning to other entities such as other vehicle systems (e.g., the vehicle system 302) of the potentially damaged section of the route 108. The signaling devices can be, but not limited to, a light, a motorized gate arm (e.g., motorized motion in a vertical plane), an audible warning device, among others.

In another example, the device 304 can be utilized with PTC. PTC can refer to communication-based/processor-based vehicle control technology that provides a system capable of reliably and functionally preventing collisions between vehicle systems, over speed derailments, incursions into established work zone limits, and the movement of a vehicle system through a route switch in the improper position. PTC systems can perform other additional specified functions. Such a PTC device 304 can provide warnings to the second vehicle system 204 that cause the second vehicle system 204 to automatically slow and/or stop, among other responsive actions, when the second vehicle system 204 approaches the location of the potentially damaged section of the route 108.

In another example, the wayside device 304 can act as a beacon or other transmitting or broadcasting device other than a PTC device that communicates warnings to other vehicles or vehicle systems traveling on the route 108 of the identified section of the route 108 that is potentially damaged.

The control unit 206 and/or identification unit 220 may communicate a repair signal to an off-board facility 306 in response to identifying a section of the route 108 as being potentially damaged. The facility 306 can represent a location, such as a dispatch or repair center, that is located off-board of the vehicle systems 202, 204. The repair signal may include or represent a request for further inspection and/or repair of the route 108 at the potentially damaged section. Upon receipt of the repair signal, the facility 306 may dispatch one or more persons and/or equipment to the location of the potentially damaged section of the route 108 in order to inspect and/or repair the route 108 at the location.

Additionally or alternatively, the control unit 206 and/or identification unit 220 may notify an operator of the vehicle system of the potentially damaged section of the route 108 and suggest the operator initiate one or more of the responsive actions described herein.

In another embodiment, the examining system 200 may identify the potentially damaged section of the route 108 using the wayside device 304. For example, the detection device 230, the detection unit 218, and the communication unit 222 may be located at or included in the wayside device 304. The control unit 206 on the vehicle system may determine when the vehicle system is within a designated distance of the wayside device 304 based on an input or known location of the wayside device 304 and the monitored location of the vehicle system (e.g., from data obtained from a location determination unit). Upon traveling within a designated distance of the wayside device 304, the control unit 206 may cause the examination signal to be injected into the route 108. The wayside device 304 can monitor one or more electrical characteristics of the route 108 similar to the second vehicle 204 described above. If the electrical characteristics indicate that the section of the route 108 between the vehicle system and the wayside device 304 is damaged or broken, the wayside device 304 can initiate one or more responsive actions, such as by directing the vehicle system to automatically slow down and/or stop, warning other vehicle systems traveling on the route 108, requesting inspection and/or repair of the potentially damaged section of the route 108, and the like.

Figure 5:
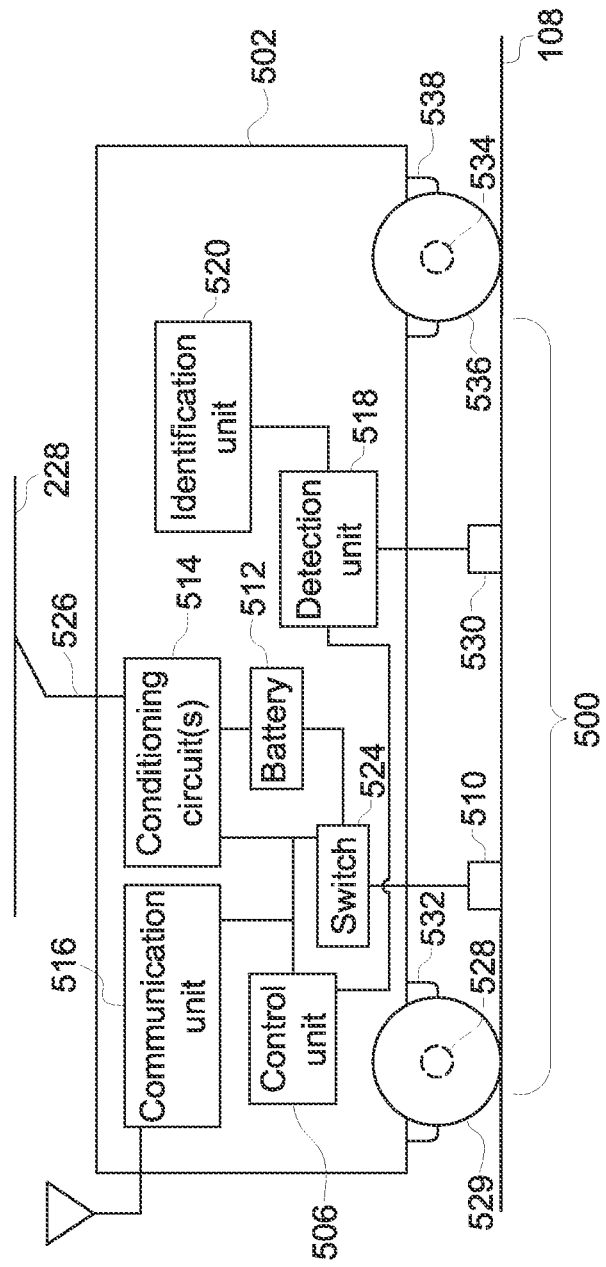
FIG. 5 is a schematic illustration of an embodiment of an examining system.

FIG. 5 is a schematic illustration of an embodiment of an examining system 500. The examining system 500 may represent the examining system 102 shown in FIG. 1. In contrast to the examining system 200 shown in FIG. 2, the examining system 500 is disposed within a single vehicle 502 in a vehicle system that may include one or more additional vehicles mechanically coupled with the vehicle 502. The vehicle 502 may represent a vehicle 104 and/or 106 of the vehicle system 100 shown in FIG. 1.

The examining system 500 includes several components described below that are disposed onboard the vehicle 502.

For example, the illustrated embodiment of the examining system 500 includes a control unit 508 (which may be similar to or represent the control unit 208 shown in FIG. 2), an application device 510 (which may be similar to or represent the application device 210 shown in Figure), an onboard power source 512 ("Battery" in FIG. 5, which may be similar to or represent the power source 212 shown in FIG. 2), one or more conditioning circuits 514 (which may be similar to or represent the circuits 214 shown in FIG. 2), a communication unit 516 (which may be similar to or represent the communication unit 216 shown in FIG. 2), and one or more switches 524 (which may be similar to or represent the switches 224 shown in FIG. 2). The examining system 500 also includes a detection unit 518 (which may be similar to or represent the detection unit 218 shown in FIG. 2), an identification unit 520 (which may be similar to or represent the identification unit 220 shown in FIG. 2), and a detection device 530 (which may be similar to or represent the detection device 230 shown in FIG. 2). As shown in FIG. 5, these components of the examining system 500 are disposed onboard a single vehicle 502 of a vehicle system.

As described above, the control unit 506 controls supply of electric current to the application device 510 that engages or is inductively coupled with the route 108 as the vehicle 502 travels along the route 108. The application device 510 is conductively coupled with the switch 524 that is controlled by the control unit 506 so that the control unit 506 can turn on or off the flow of electric current through the application device 510 to the route 108. The power source 512 is coupled with the switch 524 so that the control unit 506 can control when the electric energy stored in the power source 512 and/or the electric current generated by the power source 512 is conveyed as electric current to the route 108 via the application device 510.

The conditioning circuit 514 may be coupled with a connecting assembly 526 that is similar to or represents the connecting assembly 226 shown in FIG. 2. The connecting assembly 526 receives electric current from an off-board source, such as the electrified conductive pathway 228. Electric current can be conveyed from the electrified portion of the route 108 through the connecting assembly 526 and to the conditioning circuit 514.

The electric current that is conveyed to the conditioning circuit 514 from the power source 512 and/or the off-board source can be altered by the conditioning circuit 514. The modified current can be the examination signal that is electrically injected into the route 108 by the application device 510. Optionally, the control unit 506 can form the examination signal by controlling the switch 524, as described above. Optionally, the control unit 506 may control the conditioning circuit 514 to form the examination signal, also as described above.

The examination signal is conducted through the application device 510 to the route 108, and is electrically injected into a conductive portion of the route 108. The conductive portion of the route 108 that extends between the application device 510 and the detection device 530 of the vehicle 502 during travel may form a track circuit through which the examination signal may be conducted.

The control unit 506 may include or represent the manager component described in the '843 Application. For example, the control unit 506 may represent the manager component 210 in the '843 Application. Such a manager component can be configured to activate a transmission of electric current into the route 108 via the application device 510. In another instance, the manager component can activate or deactivate a transfer of the portion of power from the onboard and/or off-board power source to the application device 510, such as by controlling the switch and/or conditioning circuit. Moreover, the manager component can adjust parameter(s) associated with the portion of power that is transferred to the route 108.

The detection unit 518 monitors the route 108 to attempt to detect the examination signal that is injected into the route 108 by the application device 510. In one aspect, the detection unit 518 may follow behind the application device 510 along a direction of travel of the vehicle 502. The detection unit 518 is coupled with the detection device 530 that engages or is inductively coupled with the route 108, as described above.

The detection unit 518 monitors one or more electrical characteristics of the route 108 using the detection device 530. The detection unit 518 may compare the received signal that is conducted from the route 108 into the detection device 530 with this designated signal in order to measure a signal-to-noise ratio of the received signal. The detection unit 518 determines one or more electrical characteristics of the signal by the detection device 530 from the route 108 and reports the characteristics of the received signal to the identification unit 520. If no signal is received by the detection device 530, then the detection unit 518 may report the absence of such a signal to the identification unit 520. In an embodiment, the detection unit 518 may determine the characteristics of the signals received by the detection device 530 in response to a notification received from the control unit 506, as described above.

The detection unit 518 may begin monitoring signals received by the detection device 530. For example, the detection unit 518 may not begin or resume monitoring the received signals of the detection device 530 unless or until the detection unit 518 is instructed that the control unit 506 is causing the injection of the examination signal into the route 108. Alternatively or additionally, the detection unit 518 may periodically monitor the detection device 530 for received signals and/or may monitor the detection device 530 for received signals upon being manually prompted by an operator of the examining system 500.

In one aspect, the application device 510 includes a first axle 528 and/or a first wheel 529 that is connected to the axle 528 of the vehicle 502. The axle 528 and wheel 529 may be connected to a first truck 532 of the vehicle 502. The application device 510 may be conductively coupled with the route 108 (e.g., by directly engaging the route 108) to inject the examination signal into the route 108 via the axle 528 and the wheel 529, or via the wheel 529 alone. The detection device 530 may include a second axle 534 and/or a second wheel 536 that is connected to the axle 534 of the vehicle 502. The axle 534 and wheel 536 may be connected to a second truck 538 of the vehicle 502. The detection device 530 may monitor the electrical characteristics of the route 108 via the axle 534 and the wheel 536, or via the wheel 536 alone. Optionally, the axle 534 and/or wheel 536 may inject the signal while the other axle 528 and/or wheel 529 monitors the electrical characteristics.

The identification unit 520 receives the characteristics of the received signal from the detection unit 518 and determines if the characteristics indicate receipt of all or a portion of the examination signal injected into the route 108 by the application device 510. The identification unit 520 examines the characteristics and determines if the characteristics indicate that the section of the route 108 disposed between the application device 510 and the detection device 530 is damaged or at least partially damaged, as described above.

The identification unit 520 may include or be communicatively coupled with a location determining unit that can determine the location of the vehicle 502. The distance between the application device 510 and the detection device 530 along the length of the vehicle 502 may be known to the identification unit 520, such as by inputting the distance into the identification unit 520 using one or more input devices and/or via the communication unit 516.

The identification unit 520 can identify which section of the route 108 is potentially damaged based on the location of the vehicle 502 during transmission of the examination signal through the route 108, the direction of travel of the vehicle 502, the speed of the vehicle 502, and/or a speed of propagation of the examination signal through the route 108, as described above.

One or more responsive actions may be initiated when the potentially damaged section of the route 108 is identified. For example, in response to identifying the potentially damaged portion of the route 108, the identification unit 520 may notify the control unit 506. The control unit 506 and/or the identification unit 520 can automatically slow down or stop movement of the vehicle 502 and/or the vehicle system that includes the vehicle 502. For example, the control unit 506 and/or identification unit 520 can be communicatively coupled with one or more propulsion systems (e.g., engines, alternators/generators, motors, and the like) of one or more of the propulsion-generating vehicles in the vehicle system. The control unit 506 and/or identification unit 520 may automatically direct the propulsion systems to slow down and/or stop.

Figure 4:
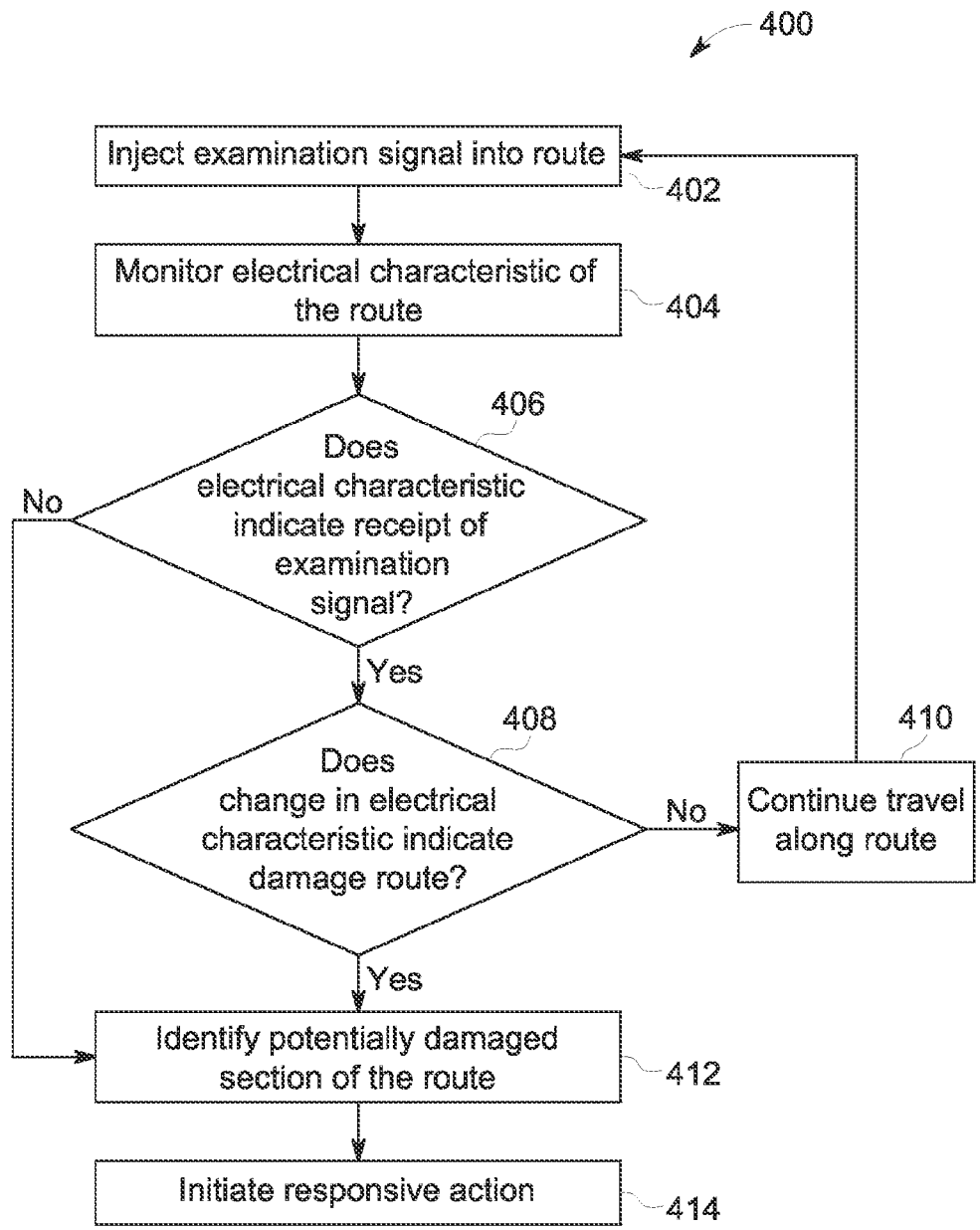
FIG. 4 is a flowchart of an embodiment of a method for examining a route being traveled by a vehicle system from onboard the vehicle system.

FIG. 4 is a flowchart of an embodiment of a method 400 for examining a route being traveled by a vehicle system from onboard the vehicle system. The method 400 may be used in conjunction with one or more embodiments of the vehicle systems and/or examining systems described herein. Alternatively, the method 400 may be implemented with another system.

At 402, an examination signal is injected into the route being traveled by the vehicle system at a first vehicle. For example, a direct current, alternating current, RF signal, or another signal may be conductively and/or inductively injected into a conductive portion of the route 108, such as a track of the route 108.

At 404, one or more electrical characteristics of the route are monitored at another, second vehicle in the same vehicle system. For example, the route 108 may be monitored to determine if any voltage or current is being conducted by the route 108.

At 406, a determination is made as to whether the one or more monitored electrical characteristics indicate receipt of the examination signal. For example, if a direct current, alternating current, or RF signal is detected in the route 108, then the detected current or signal may indicate that the examination signal is conducted through the route 108 from the first vehicle to the second vehicle in the same vehicle system. As a result, the route 108 may be substantially intact between the first and second vehicles. Optionally, the examination signal may be conducted through the route 108 between components joined to the same vehicle. As a result, the route 108 may be substantially intact between the components of the same vehicle. Flow of the method 400 may proceed to 408. On the other hand, if no direct current, alternating current, or RF signal is detected in the route 108, then the absence of the current or signal may indicate that the examination signal is not conducted through the route 108 from the first vehicle to the second vehicle in the same vehicle system or between components of the same vehicle. As a result, the route 108 may be broken between the first and second vehicles, or between the components of the same vehicle. Flow of the method 400 may then proceed to 412.

At 408, a determination is made as to whether a change in the one or more monitored electrical characteristics indicates damage to the route. For example, a change in the examination signal between when the signal was injected into the route 108 and when the examination signal is detected may be determined. This change may reflect a decrease in voltage, a decrease in amps, a change in frequency and/or phase, a decrease in a signal-to-noise ratio, or the like. The change can indicate that the examination signal was conducted through the route 108, but that damage to the route 108 may have altered the signal. For example, if the change in voltage, amps, frequency, phase, signal-to-noise ratio, or the like, of the injected examination signal to the detected examination signal exceeds a designated threshold amount (or if the monitored characteristic decreased below a designated threshold), then the change may indicate damage to the route 108, but not a complete break in the route 108. As a result, flow of the method 400 can proceed to 412.

On the other hand, if the change in voltage, amps, frequency, phase, signal-to-noise ratio, or the like, of the injected examination signal to the detected examination signal does not exceed the designated threshold amount (and/or if the monitored characteristic does not decrease below a designated threshold), then the change may not indicate damage to the route 108. As a result, flow of the method 400 can proceed to 410.

At 410, the section of the route that is between the first and second vehicles in the vehicle system or between the components of the same vehicle is not identified as potentially damaged, and the vehicle system may continue to travel along the route. Additionally examination signals may be injected into the route at other locations as the vehicle system moves along the route.

At 412, the section of the route that is or was disposed between the first and second vehicles, or between the components of the same vehicle, is identified as a potentially damaged section of the route. For example, due to the failure of the examination signal to be detected and/or the change in the examination signal that is detected, the route may be broken and/or damaged between the first vehicle and the second vehicle, or between the components of the same vehicle.

At 414, one or more responsive actions may be initiated in response to identifying the potentially damaged section of the route. As described above, these actions can include, but are not limited to, automatically and/or manually slowing or stopping movement of the vehicle system, warning other vehicle systems about the potentially damaged section of the route, notifying wayside devices of the potentially damaged section of the route, requesting inspection and/or repair of the potentially damaged section of the route, and the like.

Figure 6:
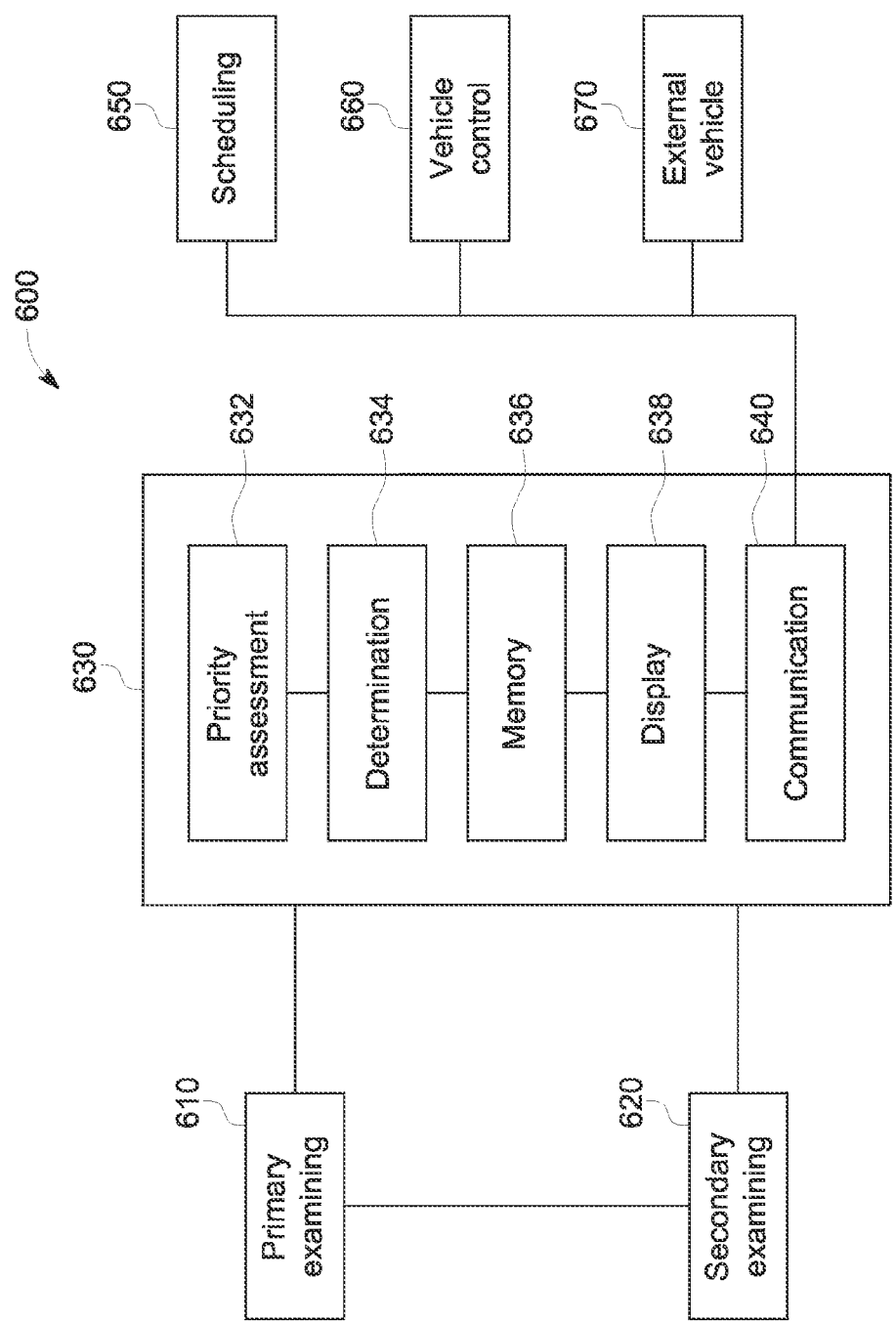
FIG. 6 is a schematic illustration of an embodiment of an examining and mitigation system.

FIG. 6 is a schematic illustration of an embodiment of an examining and mitigation system 600. The depicted examining and mitigation system 600 includes a primary examining module 610, a secondary examining module 620, and a mitigation module 630. In some embodiments, the primary examining module 610, the secondary examining module 620, and the mitigation module 630 are disposed onboard a common vehicle, or on plural vehicles of a common vehicle system. In other, one or more aspects of the secondary examining module 620 and/or the mitigation module 630, for example, may be disposed off-board, for example on a different vehicle system than the primary examining module 610 or at a wayside station, scheduling or dispatch station, or the like.

Generally, in various embodiments, the primary examining module 610 examines a route using a first technique to identify potentially damaged areas of the route, while the secondary examining module 620 (or verification module or system) uses one or more second techniques to verify whether or not a section of the route identified by the primary examining module 610 is actually damaged (or if the initial identification by the primary examining module 610 corresponds to a false positive or false alarm) and/or assess damage to the identified section of the route in more detail. Responsive to the identification or determination of damage by the first examining module 610 and/or second examining module 620, the mitigation module 630 determines an appropriate mitigation activity (or activities) and implements the mitigation activity (or activities). In various embodiments, the mitigation module 630 may be communicably coupled, for example, with one or more of a scheduling station 650 (e.g., dispatch or other station configured to schedule travel of one or more vehicle, schedule maintenance or repair activities to a route, or the like), additional vehicles of a common vehicle system (e.g., vehicles within a consist) that includes a vehicle on which the mitigation module 630 is disposed, or an external vehicle system 670 (e.g., a rail vehicle system traveling the same route but at a different point along the route, a rail vehicle system traveling an adjacent or nearby route that may be impacted by any derailment). In various embodiments, the examining and mitigation system 600 may be configured for use with one or more rail vehicles traversing a track; however, in other embodiments other types of vehicles or routes may be employed.

It should be noted that the particular arrangement depicted in FIG. 6 is meant by way of example and not exclusion, and that one or more aspects of the examining and mitigation system 600 may be eliminated, one or more aspects of a module may be incorporated into another module or separated, and/or one or more additional or alternative modules may be employed. For example, in various embodiments more than one secondary examining module 620 may be employed, while in other embodiments no secondary examining module may be employed. As another example, in some embodiments, the secondary examining module 620 may automatically examine a section of a route responsive to an initial identification by the primary examining module; however in other embodiments, the primary examining module 610 may transmit an initial identification to the mitigation module 620 which may perform a mitigation activity or may forward the identification to the secondary examining module 620 based on the initial identification. Thus, some mitigation activities may be performed based on potential damage as identified by the primary examining module 610 while other mitigation activities may be performed based on actual or confirmed damage as confirmed by the secondary examining module 620.

As indicated above, in the illustrated embodiment, the primary examining module 610 is configured to be disposed onboard a vehicle system, and to identify a section of a route being traversed by the vehicle system corresponding to at least one of a potentially damaged section of the route or an actually damaged section of the route. (As used herein, "potentially" damaged sections of track may be understood as including actually damaged sections of track as well as false positives or false alarms provided by the primary examining module. "Actually" damaged sections of track may be understood as including sections of track that are in fact damaged and/or are confirmed as damaged by one or more secondary analyses performed in addition to an initial identification by the primary examining module 610.) In various embodiments, the primary examining module 610 may be configured generally similarly to various aspects of embodiments discussed above in connection with FIGS. 1-5.

For example, the primary examining module 610 may include an application device configured to be disposed onboard a vehicle system, to be at least one of conductively or inductively coupled with the route during travel along the route, and to inject an examination signal into the route. The primary examining module 610 may also include a detection unit configured to monitor one or more electrical characteristics of the route in response to the examination signal injected into the route by the application device, as well as an identification unit configured to examine the one or more electrical characteristics of the route in order to determine whether a section of the route extending between the application device and the detection unit is potentially damaged based on the one or more electrical characteristics. Once the primary examining module 610 has made an initial determination or identification of a potentially damaged section of track, the primary examining module 610 may communicate the identification to one or both of the secondary examining module 620 or the mitigation module 630.

In the illustrated embodiment, the secondary examining module 620 is configured to at least one of determine whether a section of track initially identified by the primary examining module is actually damaged, to identify a type of damage to an identified or confirmed section of track, or to assess a level of damage to an identified or confirmed section of track. For example, the secondary examining module 620 may confirm (or exclude) an initial determination of potential damage, determine a level of damage (e.g., a depth and/or width of a break, crack, or fissure), or identify a type of damage (e.g., transverse fissure, detail fracture, or base break) responsive to an identification of the section of track by the primary examining module 610. As another example, the secondary examining module 620 may confirm (or exclude) an initial determination of potential damage, determine a level of damage, or identify a type of damage responsive to a request or command from the mitigation module 630, for example as part of a mitigating action or actions implemented by the mitigation module 630. The secondary examining module 620 may utilize a different technique than the first examining module 610 to examine one or more sections of a route.

Generally, the mitigation module 630 is configured to automatically perform a mitigation action corresponding to a section of the route responsive to an identification of potential or confirmed damage to the route by the primary examining module 610 and/or the second examining module 620. As one example, the mitigation module 630 may be configured to provide an automatic notification to an operator of a vehicle system to perform a mitigation task. As another example, the mitigation module 630 may be configured to perform a mitigation action autonomously without operator intervention. In some embodiments, the mitigation module 630 may be configured to transmit a mitigation communication to a trip planning module that is configured to adjust a trip plan for a vehicle system responsive to receipt of the mitigation communication from the mitigation module. The mitigation module 630 may further be configured to assess a type and/or an extent of damage, and to determine an appropriate mitigation response based on the type and/or extent of damage. The mitigation module 630 may be configured to identify and/or implement a mitigation activity to be performed internally (e.g., by a vehicle system on which the mitigation module 630 is disposed) or externally (e.g., by a scheduling station or vehicle system remote from the mitigation module 630, or on which the mitigation module 630 is not disposed).

The mitigation module 630 depicted in FIG. 6 includes a priority assessment module 632, a determination module 634, a memory 636, a display module 638, and a communication module 640. Generally, in various embodiments, the mitigation module 630 may be configured to one or more of provide an alarm and/or instruction to an operator and/or dispatcher; to slow or stop a vehicle on which the mitigation module 630 is disposed; to slow, stop, or re-route another vehicle system (e.g., a following vehicle system on the same route and/or or a vehicle traversing an adjacent route); or to schedule a maintenance, repair, or replacement activity. In some embodiments, the mitigation action may be specified by a general rule (e.g., stop the vehicle upon a particular determined type or extent of damage to a route, slow the vehicle a specified amount upon a particular determined type or extent of damage to a route, or the like). Additionally or alternatively, the mitigation action may be tailored to a particular vehicle and/or route. For example, a characteristic of the vehicle (length, weight, handling capabilities, braking capabilities, or the like) or a characteristic of the route (route condition, grade, curvature, or the like) may be utilized to tailor a mitigation action to a particular set of circumstances.

In the illustrated embodiment, the priority assessment module 632 is configured to receive information from the primary examining module 610 and/or the secondary examining module 620, and to determine a relative priority of conditions corresponding to the received information. In some embodiments, the priority assessment module 632 may assign a priority level or identifier to one or more particular sections of track identified as potentially or actually damaged. Additionally or alternatively, the priority assessment module 632 may rank all pending identified sections of track in a hierarchical order based on priority.

As one example, an identification of confirmed damage by the secondary examining module 620 may receive a higher priority than an identification of potential damage by the primary examining module 610. Generally speaking, for a given identified section of a route, priority in various embodiments may increase with increases in traffic along a route or along adjacent routes, larger vehicle configuration such as length or weight, more demanding operating conditions such as higher average speed, route terrain characteristics such as increased grade and/or curvature of route, increased numbers of incidents reported or identifications made for the section of track, increased elapsed time since an initial report or identification of the section of track. One or more route quality characteristics, such as quality of tics and fasteners, may be used to determine priority as well. Additional route quality characteristics that may be assessed include whether the section of the route already on a list or schedule for maintenance or rehabilitation work, and/or any history of relatively high wear and/or derailments associated with the identified section of the track. It should be noted that databases or other sources of information (e.g., a database including identifications of sections of route scheduled for maintenance work or historical information regarding wear and/or derailments associated with a given section of a route, among others) may be maintained in one or more locations on-board the vehicle system and/or off-board the vehicle system in various embodiments. For example, in some embodiments, a database may be maintained in a central, dispatch, maintenance, or other office, and may be accessed by one or more aspects of a vehicle system via digital communications.

In the illustrated embodiment, the determination module 634 is configured to determine an appropriate mitigation action responsive to information received from the primary examining module 610 and/or the secondary examining module 620. The determination module 634 may determine one or more mitigation actions based on, for example, type of damage, level of damage, or a priority level assigned by the priority assessment module 632. Additionally or alternatively, the determination module 634 may determine one or more mitigation activities based on a level of confidence. For example, a section of track for which an otherwise low priority identification has been made may be treated as a higher priority identification if there is a relatively low level of confidence in the assessment of the level of damage to the track.

In various embodiments, the determination module 634 may be configured to select the mitigation action from plural potential actions based at least upon a priority level corresponding to the identified section of track (e.g., a priority level assigned by the priority assessment module 632). The priority level may correspond to, for example, one or more of a traffic condition, a route condition, or a number of identifications of the identified section of track. As another example, the priority level may correspond to an elapsed time since an initial identification of a section of track. Generally, in various embodiments, the determination module 634 is configured to weigh priority factors for one or more identified potentially damaged sections of track, and determine one or more appropriate actions.

Mitigating actions in various embodiments may include one or more of warnings or instructions to an operator operating a vehicle system on which the primary detection module 610 is disposed; warnings or instruction to an operator operating a different vehicle system; warnings, instructions, or requests to a scheduling or dispatch station; automatic control commands to one or more vehicles of the vehicle system on which the primary detection module 610 is disposed; or automatic control commands to one or more other vehicles. One or more vehicles may be stopped, slowed, and/or re-routed as part of a mitigation activity.

In various embodiments, a characteristic of the identification of a section of track (e.g., priority level) may be used to determine the extent of a mitigation response (e.g., automatic performing of a mitigation action). For example, a lower priority identification may result in a slow-down of one or more vehicles, while a higher priority identification may result in the stoppage of one or more vehicles and/or a re-routing of one or more vehicles. Additionally or alternatively, the determining module 634 may determine or assign an order of performance between identifications of different sections of track using a characteristic of the identifications of the respective sections of track (e.g., priority level). For example, a limited mitigation resource may be allocated preferentially to sections of track having higher priority levels as determined by the priority assessment module 632. For instance, if there are limits on maintenance or inspection resources available, a first section of track having a higher priority level may be assigned to have a maintenance or inspection performed before a second section of track having a lower priority level.

In some instances, a given type of potential damage to a track may not substantially or measurably increase risk of derailment or other accident, but may develop over time to present a heightened risk. Thus, if an initial report or identification of a given section of track is determined to not merit track maintenance or alteration or modification of network travel, the identification may be tabulated and/or added to a count of reports for the given section. For example, a first identification may not result in maintenance or inspection, but a subsequent (e.g., second, third, or the like) identification may. As another example, an elapsed time since a first report may be used to determine an appropriate level and/or timing of a mitigation activity for the given section of track, as an insubstantial or immeasurable amount of damage may grow to an increased risk as a route is subject to fatigue, exposure, or the like. Thus, in various embodiments, a mitigation activity may include ongoing monitoring of a section of track and/or recording or tabulating a report of possible damage. For example, a number of subsequent reports and/or an elapsed time since an initial report may be monitored. Further, sections of track that have been identified as having negligible or minor damage may be subject to increased monitoring relative to sections of track that have not been identified at all.

In some embodiments, a mitigation activity may include transmission of a mitigation communication (e.g., a speed target to be followed) to a trip planning or other control module of one or more vehicles (e.g., a vehicle on which the primary examining module 610 is disposed and/or a different vehicle). For example, a vehicle may be configured for trip planning as set forth in U.S. patent application Ser. No. 11/608,257, filed 8 Dec. 2007, entitled "Method And Apparatus For Optimizing Railroad Train Operation For A Train Including Multiple Distributed Power Locomotives," U.S. Published Application No. 2007/0233335, the entire content of which is incorporated herein by reference. The trip planning controller may re-plan a trip to accommodate a mitigation action using information regarding the train make-up, mission objectives, and route or terrain characteristics. Thus, a trip plan for one or more vehicles may be autonomously optimized and re-planned as part of a mitigation activity, for example, to account for a reduced speed, a stoppage, or a re-route to a different path of travel. The mitigation communication may be transmitted for example to the vehicle control module 660 disposed on the same vehicle as the primary examining module 610. Additionally or alternatively, the mitigation communication may be transmitted to the external vehicle 670. The mitigation communication transmitted to the vehicle control module 660 and the external vehicle 670 may be the same or different. For example, in one example scenario, a first vehicle (including the primary examining module 610) may be traversing a section of a first track for which damage has been identified meriting stoppage of the first vehicle. A stop command may then be sent as a mitigation action to the first vehicle (and any following vehicles on the same track) to prevent derailment. A second vehicle may be traversing a different track for which there is not a risk of derailment from the identified section. However, the second vehicle may traversing an adjacent track that could be fouled or obstructed by a derailment on the first track, and a speed limit may be imposed on the second vehicle as a mitigation activity to provide the second vehicle sufficient time to stop in case the second track becomes obstructed or fouled.

The mitigation module 630 may also communicate one or more mitigating activities (and/or identifications of damaged sections of track) to the scheduling station 650. The scheduling station 650 may then schedule an inspection or maintenance activity for the identified section. Additionally, the scheduling station may transmit a request or command to stop, slow, or re-route one or more vehicles traversing the same route or a different route that may be impacted. Further, additionally or alternatively, the mitigation module 630 and/or the scheduling station 650 may communicate a command or request to a wayside station, for example, to operate a crossing or switch to prevent traffic to an identified section of track. A command or request transmitted by the mitigation module 630 may be implemented, for example, by a PTC system.

As indicated above, the determination module 634 may rank reported or identified sections of track to prioritize and target limited resources. Higher priority sections (e.g., sections having one or more of more frequent or numerous reports, older reports, more curvature, more grade, higher speed, higher weight, higher traffic level on route or adjacent route) may receive an increased level of response and/or reduced implementation time of scheduling of maintenance activities. Further, the mitigation response for a given section may be escalated based on a number of reports or time elapsed since a report.

For example, a first report or identification may result in a first level of mitigation activity of slowing a vehicle down (e.g., below a predetermined speed to mitigate risk of derailment) until more detail is obtained regarding the potential damage (by secondary examining module 620 and/or manual inspection). A subsequent report or identification of the section may result in a second level of mitigation activity of stopping and/or re-routing travel until an on-site inspection and/or maintenance may be performed. A further subsequent report may result in a third level of mitigation activity of stopping and re-routing travel until the section of track is replaces. Thus, the mitigation module 630 may be configured to perform a first mitigation action responsive to a first identification of the identified section of track, and to perform a different, second mitigation action responsive to a subsequent identification of the identified section of track. It should be noted that the above example is meant by way of illustration, and that particular priority level assignments and/or associated actions may be tailored as appropriate for individual systems or transportation networks. It may further be noted that the particular arrangement depicted if FIG. 6 is intended by way of illustration, and that other arrangement may be employed. For example, one or more aspects of the determination module 634 and the priority assessment module 632 may be combined with one or more other modules, omitted, re-assigned to a different module, or the like, and that one or more additional or alternative modules may also be employed In the illustrated embodiment, the display module 638 is configured to provide a visual and/or audible message or messages to an operator of a vehicle system on which the primary examining module 610 is disposed. For example, the display may include a screen and/or speaker to provide a written message and/or alarm to an operator. As one example, the display module 638 may provide a readable suggestion or command for an operator to implement. As another example, the display module 638 may provide a readable description of an incident of damage (potential or actual) identified. As one more example, the display module 638 may provide a readable description of a control or other mitigation activity autonomously implemented (e.g., an explanation of why the vehicle is being slowed or stopped). The display module 638 may provide a combined or tiered message, for example, an initial alarm to warn an operator of detected potential damage, and a subsequent readable display describing the detected damage and/or one or more mitigation activities that have been implemented responsive to the identification of damage to the route.

In the illustrated embodiment, the communication module 640 is configured to transmit information between the mitigation module 630 and the scheduling station 650, the vehicle control module 660, and the external vehicle 670. The communication module 640 in various embodiments may be configured communicate by one or more techniques, such as wired or wireless, by any appropriate protocol or technique. The communication module 660 for example may transmit alarms, statuses, control commands or requests to implement mitigation activities, requests for additional information, or the like between the mitigation module and the scheduling station 650, the vehicle control module 660, and the external vehicle 670.

Figure 7:
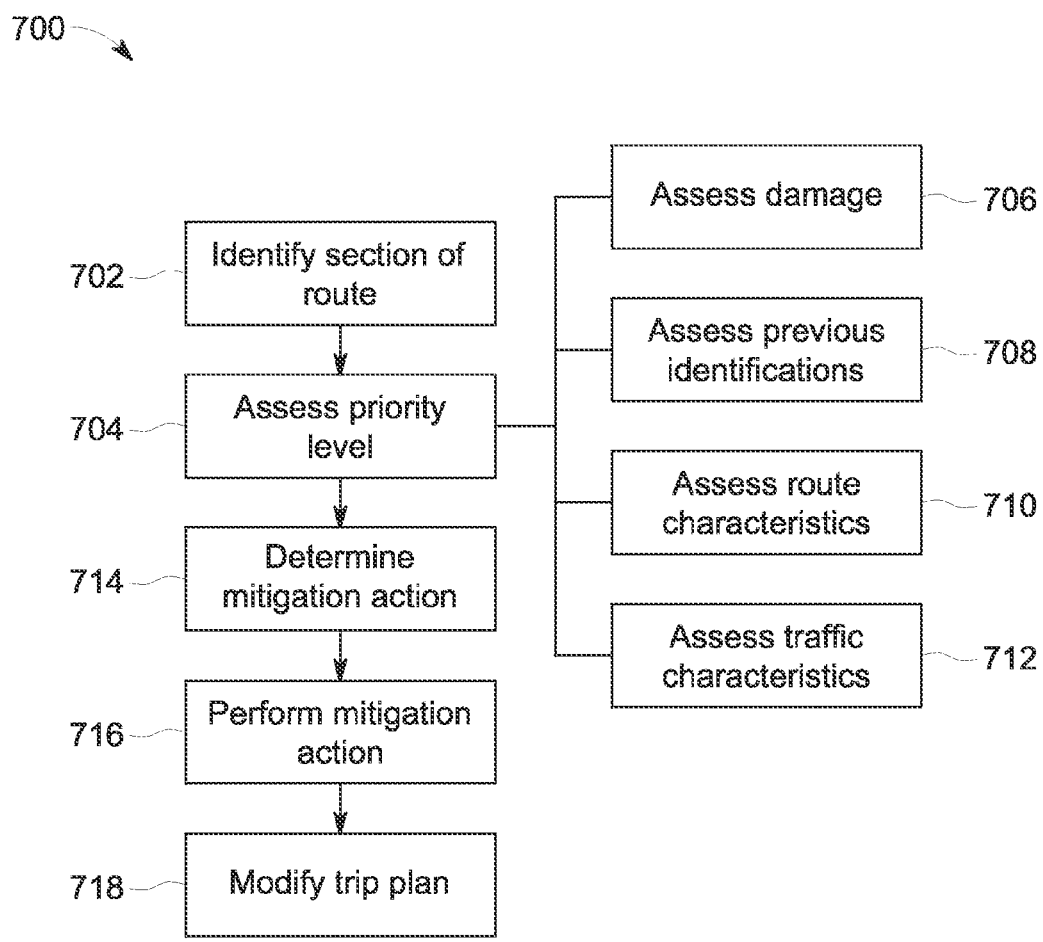
FIG. 7 is a flowchart of an embodiment of a method for examining a route being traveled by a vehicle system from onboard the vehicle system.

FIG. 7 illustrates a flowchart of a method 700 for examining a route being traveled by a vehicle system in accordance with one embodiment. The method 700 may be performed, for example, using certain components, equipment, structures, or other aspects of embodiments discussed above. For example, one or more steps or aspects of the method 400 discussed above may be combined with the method 700 in various embodiments. In certain embodiments, certain steps may be added or omitted, certain steps may be performed simultaneously or concurrently with other steps, certain steps may be performed in different order, and certain steps may be performed more than once, for example, in an iterative fashion. In various embodiments, portions, aspects, and/or variations of the method 700 may be able to be used as one or more algorithms to direct hardware to perform operations described herein. The method 700 may be used in conjunction with one or more embodiments of the vehicle systems and/or examining systems described herein. Alternatively, the method 700 may be implemented with another system.

At 702, a section of route upon which a vehicle is traveling is identified as being potentially damaged. The identification may be made or determined by one or more examining systems or modules disposed on the vehicle. For example, a primary examining system may make an initial identification of potentially damaged sections, and the secondary system may make a subsequent identification that confirms (or excludes or negates) the initial identification. The primary and secondary identifications may be made substantially simultaneously or at different times. The identification of one or more sections of track as potentially damaged (or confirmed as damaged) may be transmitted, for example, to a mitigation module (e.g., the mitigation module 630).

At 704, a priority level of the identified section of the route is assessed. For example, identifications that are not confirmed may receive a lower priority, identification that are confirmed but indicate only minor or negligible damage may receive a medium priority, and identifications that are confirmed as being substantial may assigned a higher priority. Generally, for a given section of track, factors such as a higher number of reports of potential damage, a history of track wear or accidents, higher curvature, higher grade, lower track quality, higher vehicle speed, higher vehicle weight, longer vehicle length, higher extent of damage, or the like may result in a higher priority. On the other hand, factors that may result in a lower assessed priority include if it is an initial identification of the section as potentially damaged, lower curvature, lower grade, higher track quality, lower vehicle speed, lower extent of damage, or the like. The assessment of the priority level at 704 in various embodiments, for example, may include assessments at one or more of sub-steps 706, 708, 710, and 712. It may be noted that a priority assessment for a given identification of a section of track may be changed or adjusted. As just one example, if the level of damage for an initial identification is unknown, the identification may be assigned a high priority. Then, if the level of damage is subsequently determined to be non-existent or negligible, the identification may accordingly be adjusted to a lower priority.

At 706, damage is assessed. The damage may be assessed, for example, by a secondary examining system or visual examination, among others. The damage may be assessed by type and/or by extent (e.g., a break or fissure extending completely through a track, a break or fissure extending a given percentage of the depth of the track, a width of a break or fissure, or the like). The assessment of damage may also include an assessment of whether there is any damage (e.g., confirmation of an initial identification) or not (e.g., exclusion or negation of an initial identification as a false alarm or false positive).

At 708, previous identifications are assessed. For example, if a given section of track has been identified previously, it may indicate that a condition is worsening to a point requiring an increased level of mitigation activity. Previous identifications may also be assessed in terms of elapsed time, as exposure to elements and/or fatigue from use may exacerbate a previously insubstantial amount of damage.

At 710, route characteristics are assessed. The route characteristics may pertain to the quality (e.g., quality of ties or fasteners of the identified section, age of the section, maintenance history of the section, status of the section with respect to upcoming scheduled maintenance, or the like). Additionally or alternatively, the route characteristics may pertain to the terrain or configuration of the route (e.g., curvature, grade). In various embodiments, vehicle characteristics, such as average length, weight, and/or speed, among others, ma be assessed.

At 712, traffic characteristics are assessed. The traffic characteristics may be assessed in terms of travel on the identified section of track, to determine, for example, potential for future possible damage to the route or projected rate of deterioration of the route. For example, more frequent traffic may counsel for a higher level of mitigation. The traffic characteristics may be assessed in terms of traffic on adjacent routes as well, for example to consider potential effect of damage to the route on adjacent routes such as risk of fouling or obstructing the adjacent route.

At 714, a mitigation action (or actions) is determined. The mitigation action may include a warning to one or more of an operator, a scheduling or dispatch system, or additional vehicles. The mitigation action may include a control action (e.g., a stoppage, a speed limit, or the like) to one or more vehicles. The mitigation action may include a control action to a wayside device (e.g., activate a crossing warning or switch to prevent traffic in a given area). The mitigation action may include a command or request to a scheduling system to schedule or perform a maintenance or replacement activity. In various embodiments, the mitigation action may be implemented autonomously without operator intervention. Further still, in some embodiments, the mitigation action (e.g., a speed target over a given section of track) may be implemented by a trip planning module or related controller, with the trip planning module further re-planning or modifying a trip plan based on the mitigation action or to accommodate the mitigation action. One or more mitigation actions may be determined based on a type of damage, extent of damage, or number of reports of damage to a given section of track. In various embodiments, a mitigation action may be determined based on a priority level (e.g., a priority assessed at 704). For example, a higher priority mitigation activity may be performed before a lower priority mitigation activity. As another example, a higher level of mitigation response may be provided to an identification of a section of track assessed with a higher priority (e.g., a vehicle may be slowed for a lower priority identification and stopped for a higher priority identification).

At 716, the mitigation action (or actions) is performed. In various embodiments, the mitigation action may be implemented autonomously without operator intervention. Additionally or alternatively, in some embodiments, a mitigation action may be implemented by a message provided to an operator. The mitigation action may include one or more of a stoppage of a vehicle, a re-setting of a speed target for a vehicle, a scheduling of an inspection of the section of track, or a scheduling of maintenance or replacement of the section of track, among others.

At 718, a trip plan is modified. The trip plan may be modified, for example, by a trip planning and/or control module disposed onboard a vehicle to accommodate a mitigation activity. For example, the trip plan may have been previously optimized based on a first speed target over a given section of track. However, an identification of potential damage may result in a mitigation activity that sets a different, new speed target over the given section of track. The trip planning and/or control module may then re-plan the trip to optimize the trip plan taking the new speed target over the given section of track into account.

In an embodiment, a system (e.g., a route examination and mitigation system) includes at least one examining module configured to be disposed onboard a vehicle system and a mitigation module. The at least one examining module is configured to identify an identified section of a route being traversed by the vehicle system, with the identified section corresponding to at least one of a potentially damaged section of the route or an actually damaged section of the route. The at least one examining module includes an application device configured to be disposed onboard the vehicle system and to be at least one of conductively or inductively coupled with the route during travel along the route. The at least one examining module also includes a detection unit configured to monitor one or more electrical characteristics of the route in response to an examination signal injected into the route by the application device. Also, the at least one examining module includes an identification unit configured to examine the one or more electrical characteristics of the route in order to determine whether a section of the route extending between the application device and the detection unit is potentially damaged based on the one or more electrical characteristics. The mitigation module is configured to, responsive to an identification by the at least one examining module of the identified section of the route, automatically perform a mitigation action corresponding to the identified section of the route.

In another aspect, the at least one examining module includes a primary examining module and a secondary examining module. The primary examining module includes the application device, the detection unit, and the identification unit. The secondary examining module is configured to at least one of determine whether a section of track initially identified by the primary examining module is actually damaged, to identify a type of damage, or to assess a level of damage.

In another aspect, the mitigation module is configured to provide an automatic notification to an operator of the vehicle system to perform a mitigation task.

In another aspect, the mitigation module is configured to autonomously perform the mitigation action without operator intervention.

In another aspect, the mitigation module is configured to transmit a mitigation communication to a trip planning module that is configured to adjust a trip plan for the vehicle system responsive to receipt of the mitigation communication from the mitigation module.

In another aspect, the mitigation module is disposed onboard the vehicle system.

In another aspect, the mitigation module includes a determination module configured to select the mitigation action from plural potential actions based at least upon a priority level corresponding to the identified section of track, the priority level corresponding to at least one of a traffic condition, a route condition, or a number of identifications of the identified section of track.

In another aspect, the mitigation module is configured to perform a first mitigation action responsive to a first identification of the identified section of track, and to perform a different, second mitigation action responsive to a subsequent identification of the identified section of track.

In an embodiment, a method (e.g., for examining a route being traveled by a vehicle system and performing one or more mitigating activities corresponding to one or more potentially damaged sections of the route) includes electrically injecting an examination signal into a route being traveled by a vehicle system. The examination signal is injected into the route by the vehicle system. The method also includes monitoring one or more electrical characteristics of the route responsive to the examination signal. Also, the method includes identifying, with an identification unit, a potentially damaged section of the route based on the one or more electrical characteristics. Further, the method includes performing, automatically, with a mitigation module, responsive to an identification of the potentially damaged section of the route by the identification unit, a mitigation action corresponding to the identified section of the route.

In another aspect, the method includes providing, via the mitigation module, an automatic notification to an operator of the vehicle system to perform a mitigation task.

In another aspect, the method includes autonomously performing the mitigation action without operator intervention.

In another aspect, the method includes transmitting, from the mitigation module, a mitigation communication to a trip planning module, and adjusting, with the trip planning module, a trip plan for the vehicle system responsive to receipt of the mitigation communication from the mitigation module.

In another aspect, the method includes selecting the mitigation action from plural potential actions based at least upon a priority level corresponding to the identified section of track, the priority level corresponding to at least one of a traffic condition, a route condition, or a number of identifications of the identified section of track.

In another aspect, the method includes performing a first mitigation action responsive to a first identification of the identified section of track, and performing a different, second mitigation action responsive to a subsequent identification of the identified section of track.

In an embodiment, a tangible and non-transitory computer readable medium includes one or more computer software modules configured to direct one or more processors to control electrical injection of an examination signal into a route being traveled by a vehicle system, the examination signal being injected into the route by the vehicle system. The one or more computer software modules are also configured to direct the one or more processors to monitor one or more electrical characteristics of the route responsive to the examination signal. The one or more computer software modules are also configured to direct the one or more processors to identify a potentially damaged section of the route based on the one or more electrical characteristics. The one or more computer software modules are also configured to direct the one or more processors to perform, responsive to an identification of the potentially damaged section of the route, a mitigation action corresponding to the identified section of the route.

In another aspect, the computer readable medium is further configured to direct the one or more processors to provide a notification to an operator of the vehicle system to perform a mitigation task.

In another aspect, the computer readable medium is further configured to direct the one or more processors to autonomously perform the mitigation action without operator intervention.

In another aspect, the computer readable medium is further configured to direct the one or more processors to transmit a mitigation communication to a trip planning module that is configured to adjust a trip plan for the vehicle system responsive to receipt of the mitigation communication.

In another aspect, the computer readable medium is further configured to direct the one or more processors to select the mitigation action from plural potential actions based at least upon a priority level corresponding to the identified section of track, with the priority level corresponding to at least one of a traffic condition, a route condition, or a number of identifications of the identified section of track.

In another aspect, the computer readable medium is further configured to direct the one or more processors to perform a first mitigation action responsive to a first identification of the identified section of track, and to perform a different, second mitigation action responsive to a subsequent identification of the identified section of track.

Various components and modules described herein may be implemented as part of one or more computers, computing systems, or processors. The computer, computing system, or processor may include a microprocessor. The microprocessor may be connected to a communication bus. The computer or processor may also include a memory. The memory may include Random Access Memory (RAM) and Read Only Memory (ROM). The computer or processor further may include a storage system or device, which may be a hard disk drive or a removable storage drive such as a floppy or other removable disk drive, optical disk drive, and the like. The storage system may also be other similar means for loading computer programs or other instructions into the computer or processor. The instructions may be stored on a tangible and/or non-transitory computer readable storage medium coupled to one or more servers.

As used herein, the term "computer" or "computing system" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "computing system."

The set of instructions may include various commands that instruct the computer or processor as a processing machine to perform specific operations such as the methods and processes described herein. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended clauses, along with the full scope of equivalents to which such clauses are entitled. In the appended clauses, the terms "including" and "in which" are used as the plain-English equivalents of the respective terms "comprising" and "wherein." Moreover, in the following clauses, the terms "first," "second," and "third," etc. are used merely as labels, and are not intended to impose numerical requirements on their objects. Further, the limitations of the following clauses are not written in means-plus-function format and are not intended to be interpreted based on 35 U.S.C. §112, sixth paragraph, unless and until such clause limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter may include other examples that occur to those of ordinary skill in the art. Such other examples are intended to be within the scope of the clauses if they have structural elements that do not differ from the literal language of the clauses, or if they include equivalent structural elements with insubstantial differences from the literal languages of the clauses.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "an embodiment" or "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described systems and methods without departing from the spirit and scope of the inventive subject matter herein involved, it is intended that all of the subject matter of the above description or shown in the accompanying drawings shall be interpreted merely as examples illustrating the inventive concept herein and shall not be construed as limiting the inventive subject matter.

The invention claimed is:

1. A system comprising:
    at least one examining module configured to be disposed onboard a vehicle system, the at least one examining module configured to identify an identified section of a route being traversed by the vehicle system, the identified section corresponding to at least one of a potentially damaged section of the route or an actually damaged section of the route, the at least one examining module comprising:
        an application device configured to be disposed onboard the vehicle system and to be at least one of conductively or inductively coupled with the route during travel along the route;
        a detection unit configured to monitor one or more electrical characteristics of the route in response to an examination signal injected into the route by the application device; and
        an identification unit configured to examine the one or more electrical characteristics of the route in order to determine whether a section of the route extending between the application device and the detection unit is potentially damaged based on the one or more electrical characteristics; and
    a mitigation module including a determination module that is configured to select a mitigation action from plural potential actions based at least upon a priority level corresponding to the identified section of the route, the priority level of the identified section of the route indicative of a greater priority responsive to the identified section of the route having one or more of:
        increased vehicular traffic relative to one or more other sections of the route having a lower priority,
        increased grade relative to the one or more other sections of the route having the lower priority, or
        different curvature relative to the one or more other sections of the route having the lower priority,
    wherein the mitigation module also is configured to, responsive to an identification by the at least one examining module of the identified section of the route, automatically perform the mitigation action that is selected and that corresponds to the identified section of the route, wherein the mitigation action comprises communication of a mitigation communication to a trip planning module that is configured to adjust a trip plan for the vehicle system responsive to receipt of the mitigation communication from the mitigation module.

2. The system of claim 1, wherein the at least one examining module comprises a primary examining module and a secondary examining module, the primary examining module comprising the application device, the detection unit, and the identification unit, and the secondary examining module configured to at least one of determine whether a section of the route initially identified by the primary examining module is actually damaged, to identify a type of damage, or to assess a level of damage.

3. The system of claim 1, wherein the mitigation module is configured to provide an automatic notification to an operator of the vehicle system to perform a mitigation task.

4. The system of claim 1, wherein the mitigation module is configured to autonomously perform the mitigation action without operator intervention.

5. The system of claim 1, wherein the mitigation module is disposed onboard the vehicle system.

6. The system of claim 1, wherein the mitigation module is configured to perform a first mitigation action responsive to a first identification of the identified section of the route, and to perform a different, second mitigation action responsive to a subsequent identification of the identified section of the route.

7. The system of claim 1, wherein the vehicle system is a rail vehicle system.

8. The system of claim 1, wherein the route is a track.

9. A method comprising:
    electrically injecting an examination signal into a route being traveled by a vehicle system, the examination signal being injected into the route by the vehicle system;
    monitoring one or more electrical characteristics of the route responsive to the examination signal;
    identifying, with an identification unit, a potentially damaged section of the route based on the one or more electrical characteristics;
    selecting a mitigation action from plural potential actions based at least upon a priority level corresponding to the identified section of the route, the priority level of the identified section of the route indicative of a greater priority responsive to the identified section of the route having one or more of:
        increased vehicular traffic relative to one or more other sections of the route having a lower priority,
        increased grade relative to the one or more other sections of the route having the lower priority, or
        different curvature relative to the one or more other sections of the route having the lower priority; and
    performing, automatically, with a mitigation module, responsive to an identification of the potentially damaged section of the route by the identification unit, the mitigation action that is selected and corresponding to the identified section of the route, wherein performing the mitigation action comprises communicating, from the mitigation module, a mitigation communication to a trip planning module, and adjusting, with the trip planning module, a trip plan for the vehicle system responsive to receipt of the mitigation communication from the mitigation module.

10. The method of claim 9, further comprising providing, via the mitigation module, an automatic notification to an operator of the vehicle system to perform a mitigation task.

11. The method of claim 9, further comprising autonomously performing the mitigation action without operator intervention.

12. The method of claim 9, further comprising performing a first mitigation action responsive to a first identification of the identified section of the route, and performing a different, second mitigation action responsive to a subsequent identification of the identified section of the route.

13. The method of claim 9, wherein the vehicle system is a rail vehicle system.

14. The system of claim 9, wherein the route is a track.

15. A tangible and non-transitory computer readable medium comprising one or more computer software modules configured to direct one or more processors to:
control electrical injection of an examination signal into a route being traveled by a vehicle system, the examination signal being injected into the route by the vehicle system;
monitor one or more electrical characteristics of the route responsive to the examination signal;
identify a potentially damaged section of the route based on the one or more electrical characteristics;
select a mitigation action from plural potential actions based at least upon a priority level corresponding to the identified section of the route, the priority level of the identified section of the route indicative of a greater priority responsive to the identified section of the route having one or more of:
increased vehicular traffic relative to one or more other sections of the route having a lower priority,
increased grade relative to the one or more other sections of the route having the lower priority, or
different curvature relative to the one or more other sections of the route having the lower priority; and
perform, responsive to an identification of the potentially damaged section of the route, the mitigation action that is selected and that corresponds to the identified section of the route, wherein the mitigation action includes directing the one or more processors to communicate a mitigation communication to a trip planning module configured to adjust a trip plan for the vehicle system responsive to receipt of the mitigation communication.

16. The computer readable medium of claim 15, wherein the computer readable medium is further configured to direct the one or more processors to provide a notification to an operator of the vehicle system to perform a mitigation task.

17. The computer readable medium of claim 15, wherein the computer readable medium is further configured to direct the one or more processors to autonomously perform the mitigation action without operator intervention.

18. The computer readable medium of claim 15, wherein the computer readable medium is further configured to direct the one or more processors to perform a first mitigation action responsive to a first identification of the identified section of the route, and to perform a different, second mitigation action responsive to a subsequent identification of the identified section of the route.

19. The computer readable medium of claim 15, wherein the vehicle system is a rail vehicle system.

20. The computer readable medium of claim 15, wherein the route is a track.

* * * * *